United States Patent
Maebashi et al.

(10) Patent No.: US 9,689,838 B2
(45) Date of Patent: Jun. 27, 2017

(54) ANALYTICAL CELL

(71) Applicant: HONDA MOTOR CO., LTD., Minato-ku, Tokyo (JP)

(72) Inventors: Takanori Maebashi, Wako (JP); Yoshiya Fujiwara, Wako (JP); Mitsumoto Kawai, Wako (JP); Nariaki Kuriyama, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 15/245,520

(22) Filed: Aug. 24, 2016

(65) Prior Publication Data

US 2017/0059521 A1    Mar. 2, 2017

(30) Foreign Application Priority Data

Aug. 26, 2015 (JP) ................................. 2015-166669

(51) Int. Cl.
| | |
|---|---|
| *G01N 27/00* | (2006.01) |
| *G01N 27/416* | (2006.01) |
| *H01M 14/00* | (2006.01) |
| *H01M 10/42* | (2006.01) |

(52) U.S. Cl.
CPC .... *G01N 27/4168* (2013.01); *H01M 10/4285* (2013.01); *H01M 14/00* (2013.01)

(58) Field of Classification Search
CPC .......... G01N 27/4168; H01M 10/4285; H01M 14/00
USPC .................................................. 250/440.11
See application file for complete search history.

(56) References Cited

U.S. PATENT DOCUMENTS

2010/0276277 A1*  11/2010  Chey ................... G01N 27/416
                                                    204/242

OTHER PUBLICATIONS

Unocic et al., "In-Situ Electron Microscopy of Electrical Energy Storage Materials" [online], 2011, retrieved on Jun. 15, 2015 from the Internet <http://energy.gov/sites/prod/files/2014/03/f11/es095_unocic_2011_o.pdf>.

* cited by examiner

*Primary Examiner* — Michael Maskell
(74) *Attorney, Agent, or Firm* — Carrier Blackman & Associates, P.C.; Joseph P. Carrier; William D. Blackman

(57) ABSTRACT

An analytical cell includes a first substrate with a first through hole formed therein, and a second substrate with first and second through holes formed therein. First and second solid portions protruding respectively from the first and second substrates are solid-state bonded together to form a solid state joint. By the solid state joint, the first and second substrates are joined together such that transmission membranes of the first and second substrates are mutually spaced by a predetermined distance, to form an overlapping portion. In the overlapping portion, an observation window is formed at a position where the first through holes face each other, and an accommodating part is formed between a lid member and the first substrate through the second through hole. One of negative and positive electrode active materials is provided in the accommodating part, and the other is provided between the transmission membranes of the observation window.

3 Claims, 16 Drawing Sheets

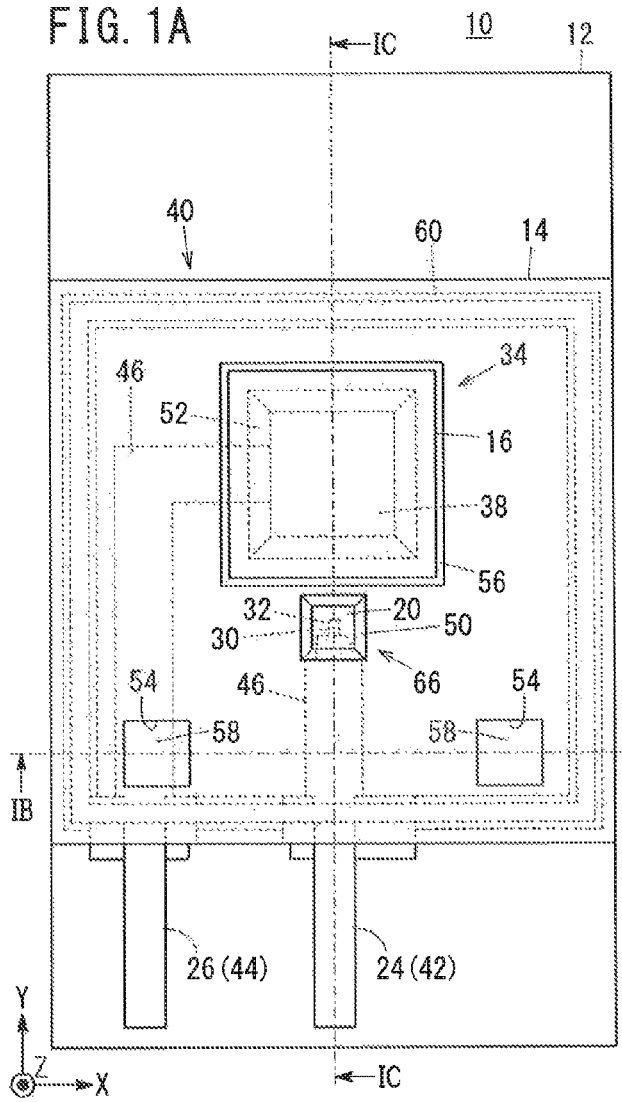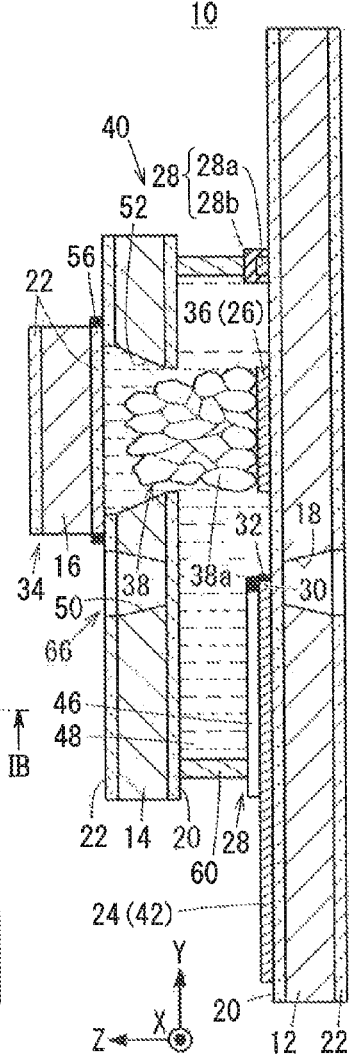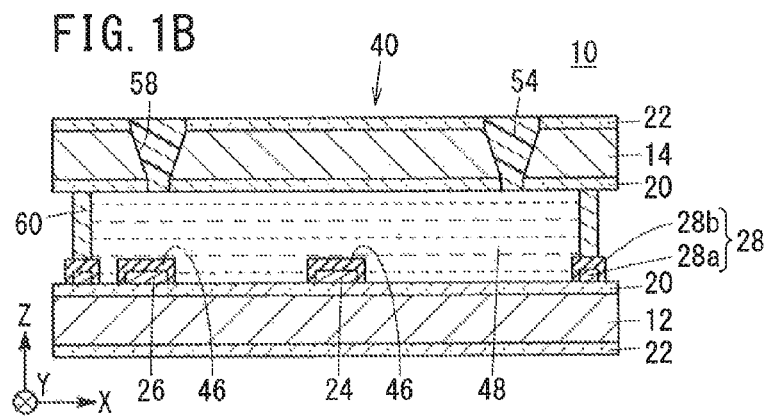

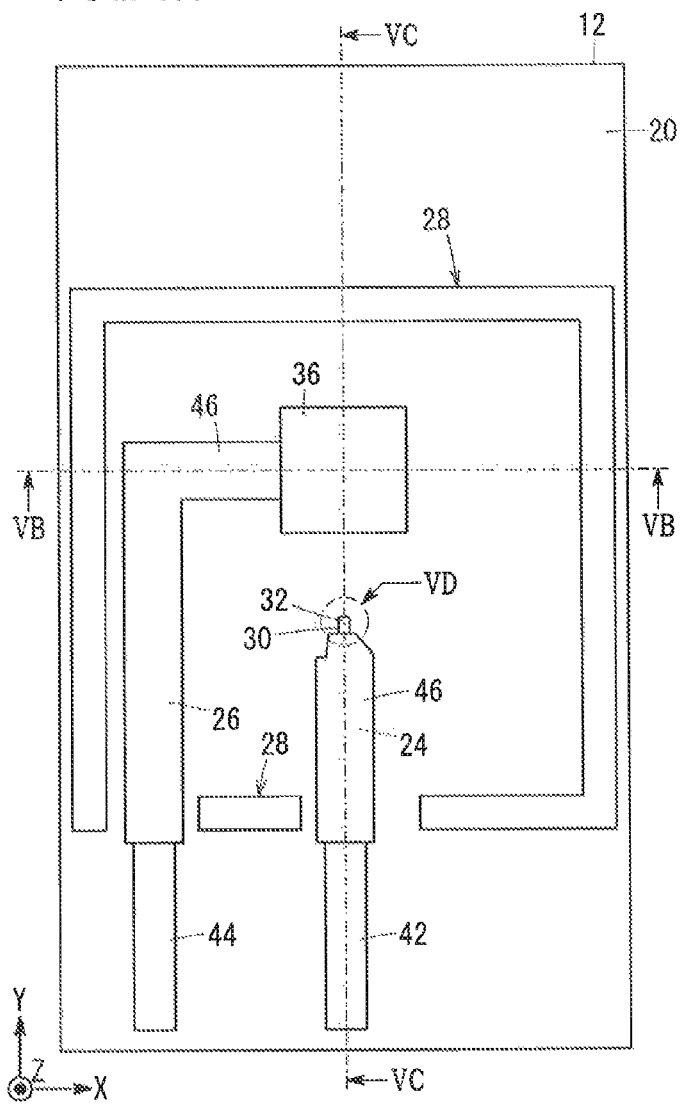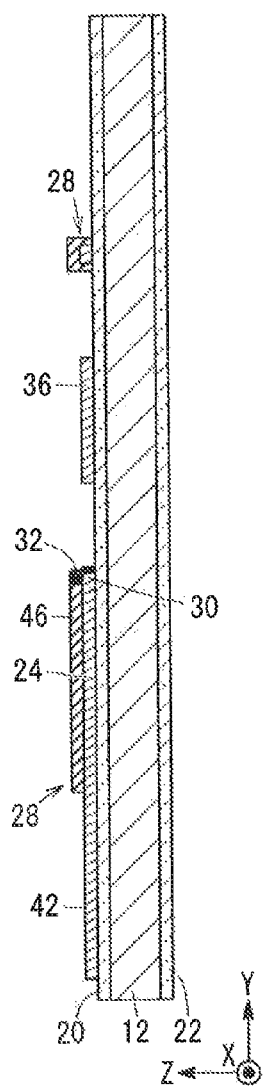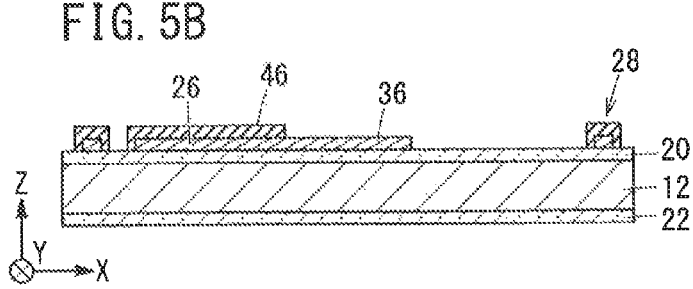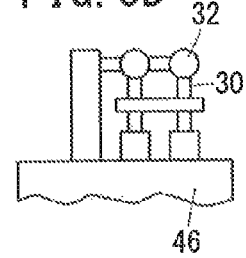

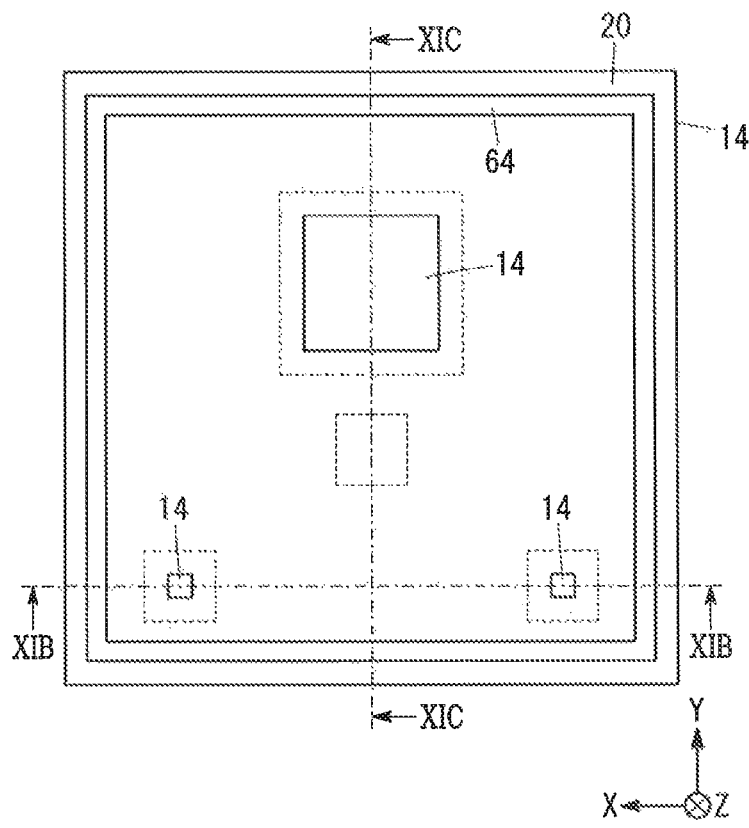
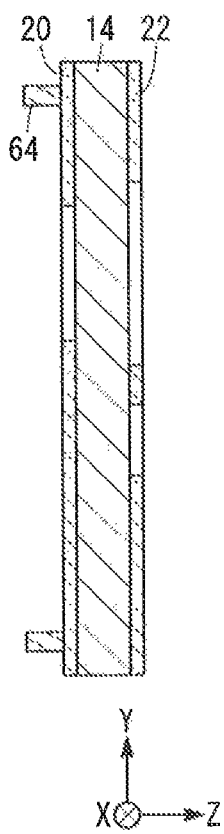
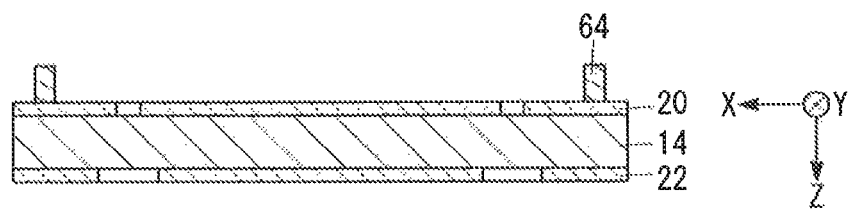
FIG. 11A
FIG. 11C
FIG. 11B

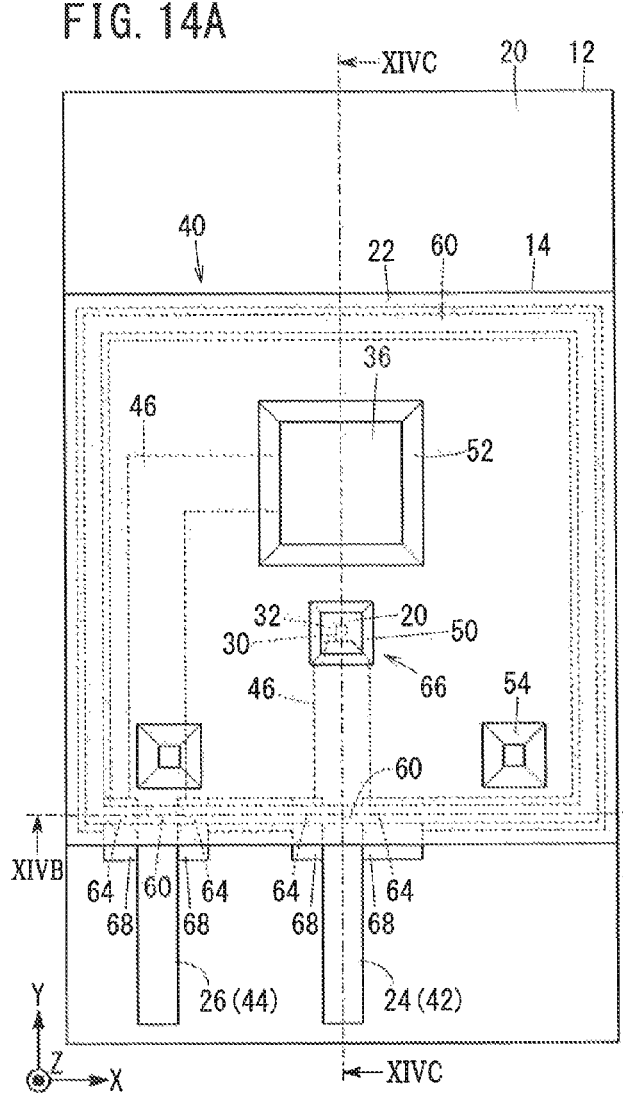
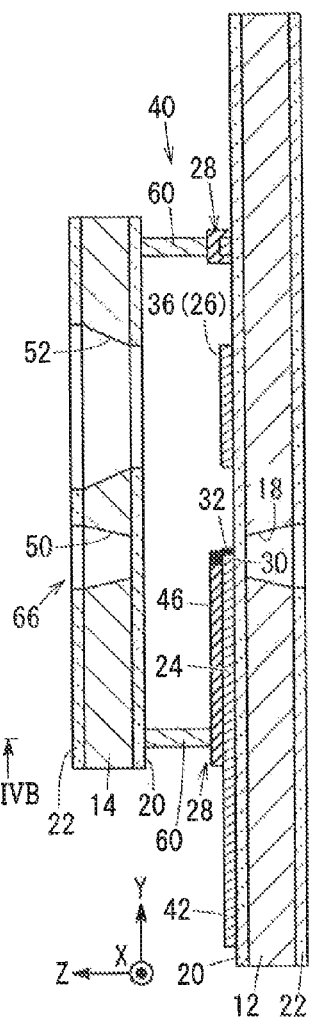
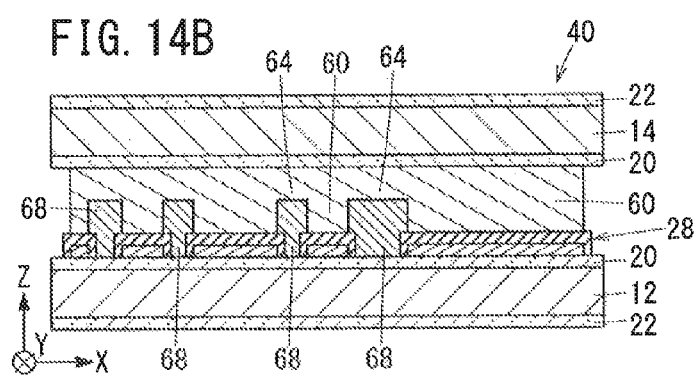

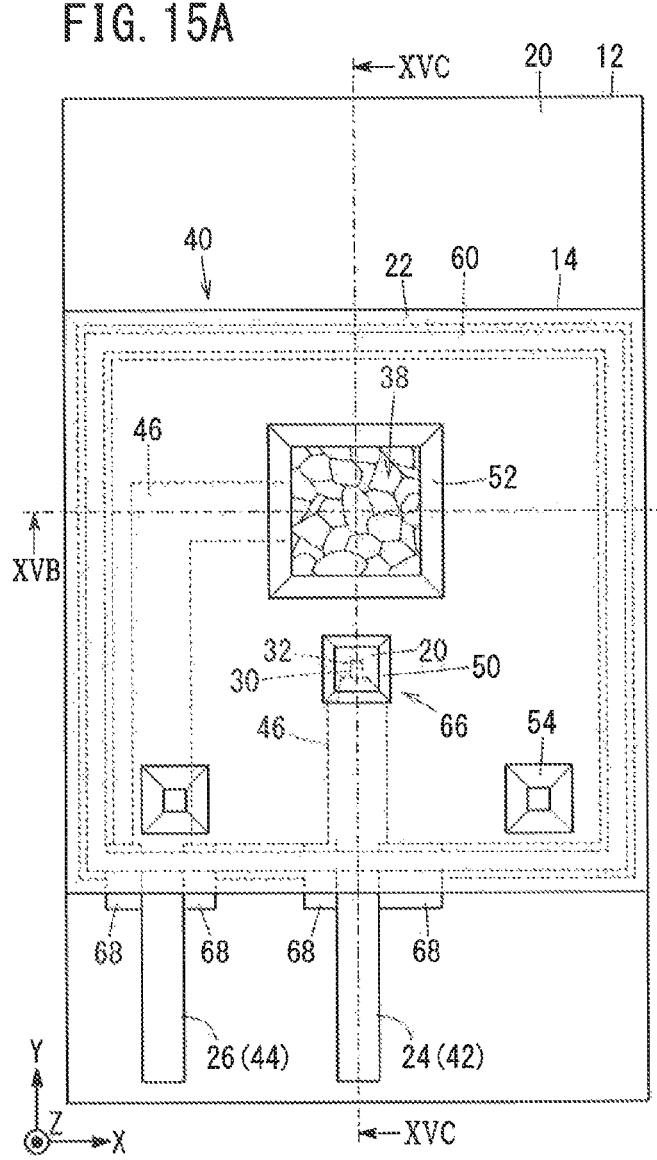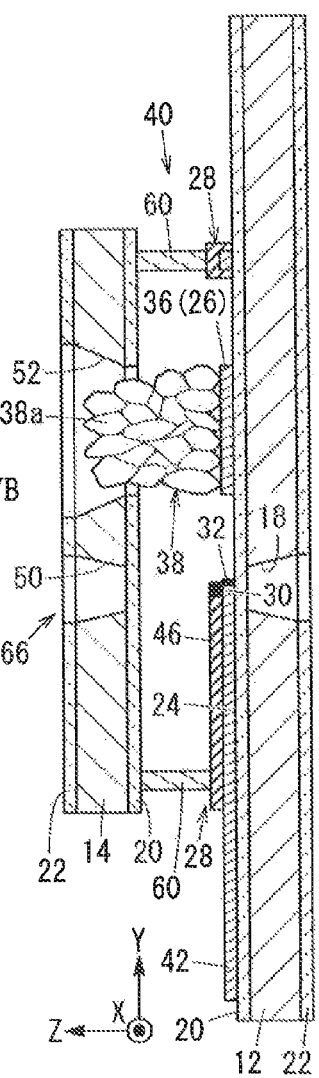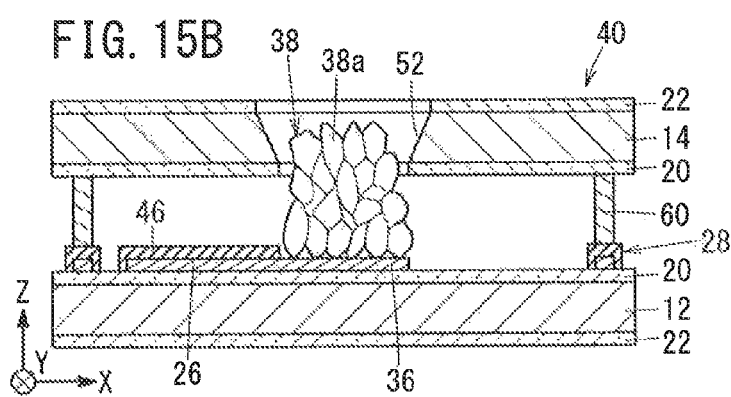

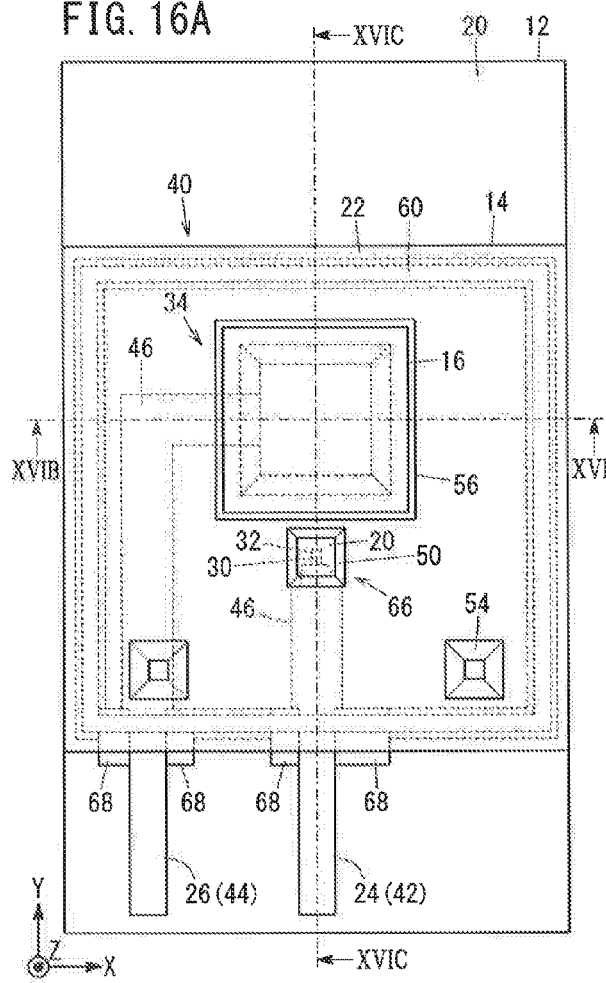
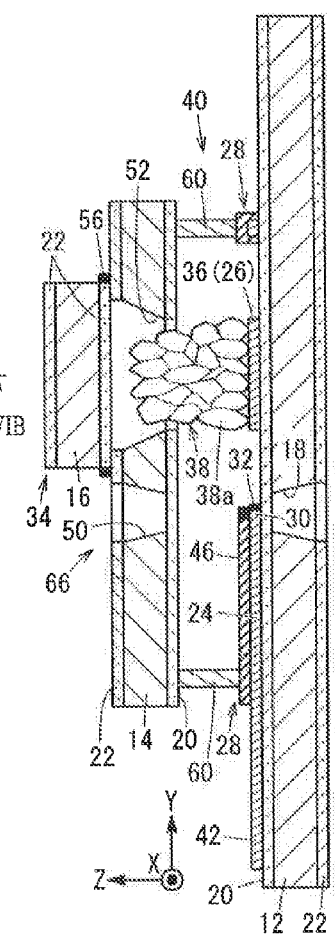
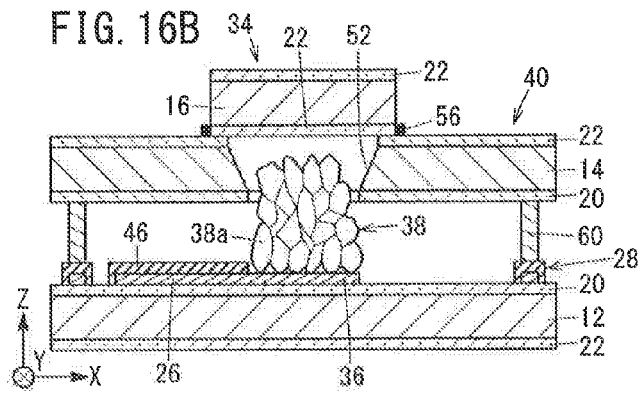

ANALYTICAL CELL

CROSS-REFERENCE TO RELATED APPLICATION

This application is based upon and claims the benefit of priority from Japanese Patent Application No. 2015-166669 filed on Aug. 26, 2015, the contents of which are incorporated herein by reference.

BACKGROUND OF THE INVENTION

Field of the Invention

The present invention relates to an analytical cell suitable for use, e.g., in an analysis of electrode reactions, etc. using analytical equipment.

Description of the Related Art

As is well known, in an electric cell, a negative electrode active material and a positive electrode active material undergo electrode reactions in a charge-discharge process. In recent years, attempts have been made to analyze such electrode reactions during the charging/discharging process using analytical equipment. For example, an analytical cell that can be observed using a transmission electron microscope (TEM) has been proposed in In-situ Electron Microscopy of Electrical Energy Storage Materials (Annual Merit Review, DOE Vehicle Technologies Program, Washington, D.C., May 9-13, 2011).

This analytical cell contains a pair of substrates (silicon substrates). Each of the substrates has a rectangular observation window having a size of about 50 μm×100 μm. The pair of substrates are partially overlapped with each other to form an overlapping portion. In the overlapping portion, the substrates are spaced from each other by a predetermined distance by a spacer interposed between the substrates. The substrates are positioned in a manner that the observation windows face each other. Further, a negative electrode active material in the form of a highly oriented graphite membrane and a positive electrode active material in the form of a $LiCoO_2$ membrane are deposited on one of the silicon substrates by an ion beam deposition method, such that the negative electrode active material and the positive electrode active material are located between the observation windows. It should be noted that each of the negative electrode active material and the positive electrode active material is extracted from a bulk body using a focused ion beam (FIB).

The negative electrode active material and the positive electrode active material are electrically connected to a negative electrode collector and a positive electrode collector (hereinafter also referred to as the "collector", collectively), respectively, inside the overlapping portion. Each of the collectors extends from the inside of the overlapping portion, such that one end side of each collector is exposed to the outside. Therefore, the negative electrode active material and the positive electrode active material can be electrically connected to the charging/discharging devices, etc. outside the overlapping portion through the collectors.

This analytical cell is observed using a transmission electron microscope (TEM), whereby it is possible to analyze the electrode reactions, etc. in the negative electrode active material and the positive electrode active material. Specifically, firstly, the analytical cell is accommodated in a front end of a holder having a flow channel for electrolytic solution inside the overlapping portion. Then, the electrolytic solution is made to flow through the flow channel of the holder into the overlapping portion, and the collectors are electrically connected to a charge-discharge tester or the like. Consequently, since the analytical cell forms a lithium ion cell, it is possible to cause electrode reactions in the negative electrode active material and the positive electrode active material. At this time, an electron beam is transmitted through the observation window for carrying out the TEM observation. In this manner, it is possible to perform the analysis of the above electrode reactions.

SUMMARY OF THE INVENTION

In the above analytical cell, active materials of graphite and $LiCoO_2$ formed into membranes by an ion beam deposition method are provided as the negative electrode active material and the positive electrode active material (hereinafter, the negative electrode active material and the positive electrode active material are also referred to as "the electrode active material", collectively), whereby the lithium ion cell is formed. However, in many practical applications of the lithium ion battery, at least one of the electrode active materials is a Li source containing Li. The electrode active material as the Li source is not formed into a membrane, but formed into particles and contained in a mixture electrode. The mixture electrode is formed by coating the collector with a mixture slurry and then drying the coated collector. The mixture slurry is obtained by dispersing the particles of electrode active materials, a conductive assistant agent, a binder (binding agent), etc. in a solvent.

That is, in the practical cell, electrode reactions are induced by adopting the mixture electrode with increased contact interface between the electrolytic solution and the electrode active materials. Therefore, in order to obtain observation results of the analytical cell under reaction conditions close to the actual reaction conditions of the practical cell, one of the electrode active materials should preferably be in the form of particles and contained in the mixture electrode.

Further, in the case of conducting a TEM observation of the analytical cell, when the electron beam is transmitted through the observation window, transmission of the electron beam tends to be obstructed by the electrolytic solution. Therefore, in the case where the distance of transmission of the electron beam through the electrolytic solution in the observation window is large, i.e., in the case where the thickness of the electrolytic solution layer of the observation window is large, the resolution of the image obtained as the observation result becomes low disadvantageously. In order to avoid the decrease in the resolution, and obtain the observation result with a high degree of accuracy, it is desirable to reduce the thickness of the electrolytic solution layer of the observation window to less than 5 μm, more preferably, to 2 μm or less.

However, the diameter of the secondary particles of the electrode active material in the above mixture electrode is in the range between several μm and more than ten μm. Therefore, in an attempt to make the reaction conditions of the analytical cell closer to the actual reaction conditions of the practical cell, if the mixture electrode instead of the electrode active material membrane is placed in the observation window, then the thickness of the electrolytic solution layer of the observation window is increased, and the observation results cannot be obtained with a high degree of accuracy.

For this reason, in the above analytical cell, it has heretofore been difficult to not only obtain the observation results under the reaction conditions close to the actual reaction conditions of the practical cell, and but also improve the observation accuracy by reducing the thickness of the electrolytic solution layer of the observation window.

A main object of the present invention is to provide an analytical cell in which it is possible to place a mixture electrode containing an electrode active material in the form of particles in an overlapping portion without increasing the thickness of an electrolytic solution layer of an observation window, and thus it is possible to obtain observation results under reaction conditions close to the actual reaction conditions of the practical cell.

According to an embodiment of the present invention, an analytical cell is provided. The analytical cell includes a first substrate and a second substrate overlapped with each other to form an overlapping portion. A negative electrode active material and a positive electrode active material are provided in the overlapping portion and separately contact electrolytic solution. An observation window for transmission of an electron beam is formed in the overlapping portion. The first substrate and the second substrate have respective first through holes extending therethrough in a thickness direction thereof. The second substrate further has a second through hole extending therethrough in the thickness direction. The first through holes are covered with respective transmission membranes respectively from one surface side of the first substrate and one surface side of the second substrate, the transmission membranes each having an electron beam permeability. The second through hole is closed by a lid member from the other surface side of the second substrate. In the overlapping portion, the first substrate and the second substrate are joined together by a solid state joint, and the transmission membrane of the first substrate and the transmission membrane of the second substrate are spaced from each other by a predetermined distance, the solid state joint being formed by solid state bonding of a first solid portion protruding from the first substrate and a second solid portion protruding from the second substrate. The first substrate and the second substrate are positioned to each other, such that the observation window is formed at a position where the first through holes face each other, and an accommodating part is formed between the lid member and the first substrate through the second through hole. One of the negative electrode active material and the positive electrode active material is provided in the accommodating part, and the other of the negative electrode active material and the positive electrode active material is provided between the transmission membranes of the observation window. A negative electrode collector and a positive electrode collector extend from the inside of the overlapping portion and protrude outside the overlapping portion, and the negative electrode collector and the positive electrode collector are electrically connected respectively to the negative electrode active material and the positive electrode active material inside the overlapping portion.

It should be noted that the term "solid state bonding (welding)" used in this specification means "General term for the method of welding performed at a temperature less than or equal to the melting point of a base material. In the method, welding of solid state materials are performed in a pressurized state or a non-pressurized state without using a brazing material." defined in JISZ3001-2 "Welding Vocabulary Part 2: Welding Processes 4.2.7. Solid State Bonding No. 22701".

In the analytical cell according to the present invention, one of the negative electrode active material and the positive electrode active material (hereinafter also referred to as the "electrode active material", collectively) is provided in an accommodating part, and the other of the negative electrode active material and the positive electrode active material is provided between the transmission membranes of the observation window. The height of the accommodating part is the distance from the first substrate to the lid member through the second through hole. Therefore, without increasing the distance between the transmission membranes of the observation window (i.e., thickness of the electrolytic solution layer of the observation window), the height of the accommodating part is increased, and the mixture electrode containing the granular electrode active material having the grain size larger than the thickness of the electrolytic solution layer of the observation window can be provided in the accommodating part. Accordingly, in this analytical cell, the reaction conditions can be made closer to the actual reaction conditions of the practical cell without degrading the resolution of the observation results.

Further, since the first substrate and the second substrate are jointed together by a solid state joint, the length of the solid state joint between the substrates becomes substantially equal to the thickness of the electrolytic solution layer of the observation window. Further, the length of the solid state joint between the substrates becomes substantially the same as the sum of the protruding lengths of the first solid portion and the second solid portion. That is, by adjusting the sum of the above protruding lengths, it is possible to make settings of the thickness of the electrolytic solution layer of the observation window easily and highly accurately. Therefore, for example, it is possible to make settings of the thickness of the electrolytic solution layer easily and highly accurately in a manner to obtain observation results at high resolution.

As described above, in the analytical cell according to the present invention, without increasing the thickness of the electrolytic solution layer of the observation window, since the mixture electrode containing the electrode active material in the form of particles can be provided in the overlapping portion, it is possible to obtain the observation result under the reaction conditions closer to the actual reaction conditions of the practical cell. Further, since the thickness of the electrolytic solution layer can be easily adjusted to a desired value with a high degree of accuracy, it is possible to improve the observation accuracy.

In the analytical cell, preferably, the solid state joint is provided to seal at least one side of the overlapping portion. In this case, by the solid state joint for joining the first substrate and the second substrate together, it is possible to seal at least one side of the overlapping portion in order to form a liquid tight space of the electrolytic solution in the overlapping portion. Thus, in this analytical cell, since the seal member for sealing the overlapping portion and the step of providing the seal member can be omitted, for example, it is possible to achieve reduction in the production cost and improvement in the production efficiency.

In the analytical cell, preferably, one of the negative electrode active material and the positive electrode active material provided in the accommodating part is formed into particles, and contained in a mixture electrode.

The above and other objects, features and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 1A is a plan view showing an analytical cell according to an embodiment of the present invention;

FIG. 1B is a sectional end view taken along a line IB-IB indicated by arrows in FIG. 1A;

FIG. 1C is a sectional end view taken along a line IC-IC indicated by arrows in FIG. 1A;

FIG. 5A is a plan view showing a state where a negative electrode active material is provided on the connector portion of the negative electrode collector in FIG. 4A;

FIG. 5B is a sectional end view taken along a line VB-VB indicated by arrows in FIG. 5A;

FIG. 5C is a sectional end view taken along a line VC-VC indicated by arrows in FIG. 5A;

FIG. 5D is an enlarged view showing the negative electrode active material and an area around the negative electrode active material, indicated by an arrow VD in FIG. 5A;

FIG. 11A is a plan view showing a state where part of the covering membrane on the second substrate in FIG. 10A that corresponds to a portion for forming a first through hole, a portion for forming the second through hole, and portions for forming the injection ports has been removed;

FIG. 11B is a sectional end view taken along a line XIB-XIB indicated by arrows in FIG. 10A;

FIG. 11C is a sectional end view taken along a line XIC-XIC indicated by arrows in FIG. 11A;

FIG. 14A is a plan view showing a state where an area which is not sealed by the solid state joint in the overlapping portion in FIG. 13A is sealed by a seal member;

FIG. 14B is a sectional end view taken along a line XIVB-XIVB indicated by arrows in FIG. 14A;

FIG. 14C is a sectional end view taken along a line XIVC-XIVC indicated by arrows in FIG. 14A;

FIG. 15A is a plan view showing a state where a mixture electrode containing a positive electrode active material in the form of particles is provided on the connector portion of the positive electrode collector in the overlapping portion in FIG. 14A;

FIG. 15B is a sectional end view taken along a line XVB-XVB indicated by arrows in FIG. 15A;

FIG. 15C is a sectional end view taken along a line XVC-XVC indicated by arrows in FIG. 15A;

FIG. 16A is a plan view showing a state where the second through hole in FIG. 15A is closed by a lid member;

FIG. 16B is a sectional end view taken along a line XVIB-XVIB indicated by arrows in FIG. 16A; and FIG. 16C is a sectional end view taken along a line XVIC-XVIC indicated by arrows in FIG. 16A.

DESCRIPTION OF THE PREFERRED EMBODIMENTS

Figure 2A:
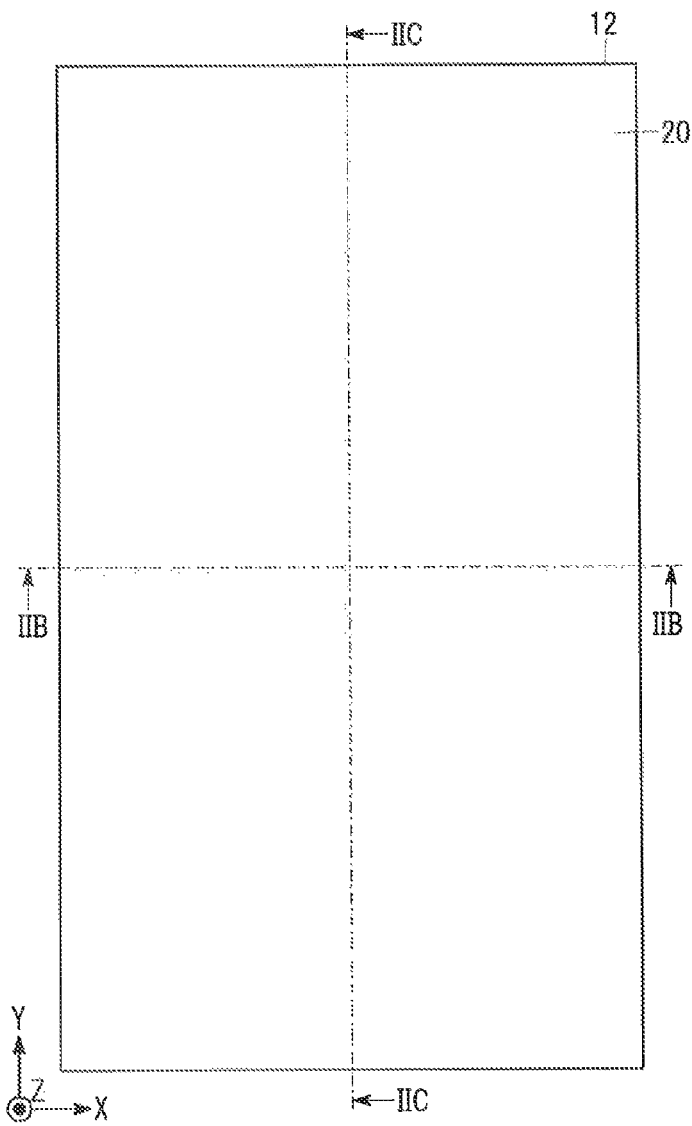
FIG. 2A is a plan view showing a transmission membrane of a first substrate having the transmission membrane on one surface and a covering membrane on the other surface.

Hereinafter, preferred embodiments of an analytical cell according to the present invention will be described in detail with reference to the accompanying drawings.

The analytical cell is suitable for use, e.g., in an analysis of electrode reactions in a negative electrode active material and a positive electrode active material based on electron beam transmission using various types of analytical equipment. For example, the analytical equipment may be a transmission electron microscope (TEM). In the case of using the TEM, the analytical cell is accommodated in a front end of a TEM holder, and an observation process is performed. Further, for example, the analytical cell may be any of a metal ion secondary cell of lithium, sodium, etc., a nickel-hydrogen cell, an alkaline-manganese cell, a metal ion air cell, a metal ion all solid cell, etc., and a fuel cell such as a solid polymer electrolyte fuel cell. Hereinafter, examples of an analytical cell made up of a lithium ion secondary cell will be described.

An analytical cell 10 according to an embodiment of the present invention will be described mainly with reference to FIGS. 1A, 1B, 1C, 7A, 7B, 7C, 12A, 12B, and 12C. In the following description, for ease of understanding the invention, the X-axis, Y-axis, and Z-axis directions shown in the drawings are defined as the width, depth, and height (thickness) directions, respectively. In addition, in the X-axis, Y-axis, and Z-axis directions, the tip of the arrow will be referred to as one end, and the base end of the arrow will be referred to as the other end.

Figure 7A:
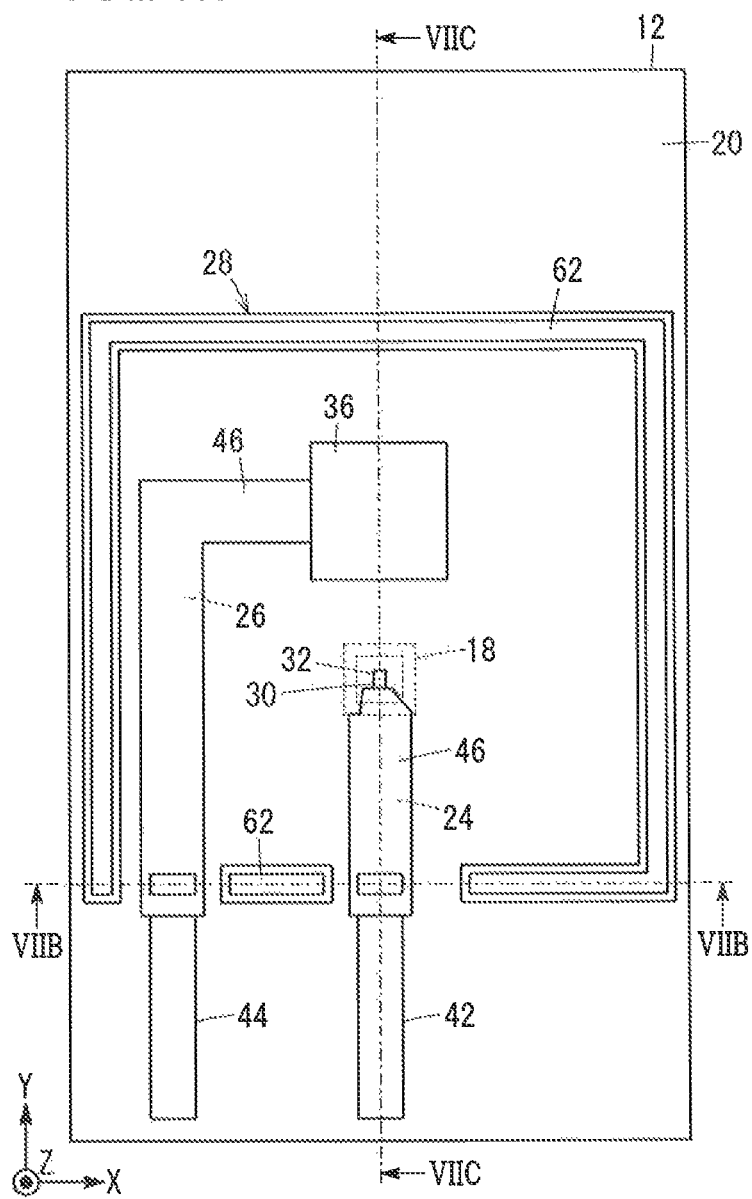
FIG. 7A is a plan view showing a state where a first through hole is formed in the first substrate in FIG. 6A.
Figure 7C:
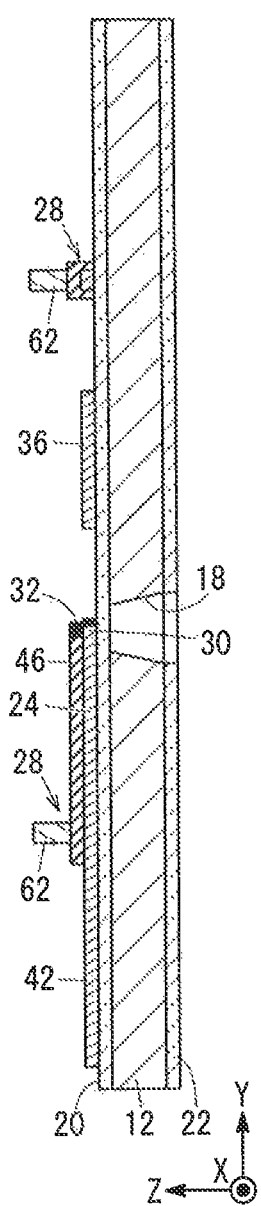
FIG. 7C is a sectional end view taken along a line VIIC-VIIC indicated by arrows in FIG. 7A.

The analytical cell 10 includes a first substrate 12, a second substrate 14, and a lid member 16. The first substrate 12 may be a substrate made of silicon (Si) with a silicon nitride ($Si_3N_4$) membrane formed thereon, a substrate made of Si with an oxide covering membrane of $SiO_2$, etc. formed thereon, or a substrate made of borosilicate glass, quartz ($SiO_2$), or the like. Further, as shown in FIGS. 1C, 7A, and 7C, a first through hole 18 is formed in the first substrate 12 at a position slightly shifted from the center of the first substrate 12 in the depth direction toward the other end. The first through hole 18 extends through the first substrate 12 in the thickness direction.

A transmission membrane 20 is provided on one surface of the first substrate 12 to cover the first through hole 18, and a covering membrane 22 is provided on the other surface of the first substrate 12 in a manner to expose the first through hole 18. The first through hole 18 has a truncated square pyramid shape which is tapered from the other surface of the first substrate 12 with the covering membrane 22 formed thereon toward the one surface thereof with the transmission membrane 20 formed thereon.

The transmission membrane 20 is made of a material having an electron beam permeability (electron beam transparency) such as silicon nitride ($Si_3N_4$), silicon carbide (SiC), etc. The covering membrane 22 may be made of the same material as the transmission membrane 20.

A negative electrode collector 24 and a positive electrode collector 26 each in the form of a layer, and a joint portion 28 are provided on the transmission membrane 20 of the first substrate 12. The material suitable for the negative electrode collector 24 includes tungsten (W), copper (Cu), stainless steel (SUS), carbon (C), etc. Further, in the negative electrode collector 24, a layered negative electrode active material 32 is disposed on a connector portion 30 (see FIG. 3D) positioned right above the first through hole 18 through the transmission membrane 20 in contact with the connector portion 30. The material suitable for forming the negative electrode active material 32 includes, for example, Li, Li alloy, $Li_4Ti_5O_{12}$, Si, Ge, Sn, Sn alloy, Al, Al alloy, Si oxide, Sn oxide, Al oxide, carbon (C), etc.

Further, this negative electrode active material 32 may have a shape and a layout configuration shown in FIG. 5D. That is, the negative electrode active material 32 may comprise six separate pieces including three types of quadrangular shape and one type of circular shape, and these pieces may be provided on the connector portion 30 of the negative electrode collector 24, or may extend across the connector portion 30 and the transmission membrane 20. In the case where the negative electrode active material 32 has the shape and the layout configuration as described above, it becomes easier to observe the behavior of deformation, etc. of the negative electrode active material 32 resulting from electrode reactions.

The material suitable for the positive electrode collector 26 includes gold (Au), platinum (Pt), carbon (C), aluminum (Al), etc. In the positive electrode collector 26, a mixture electrode 38 containing a positive electrode active material 38a in the form of particles is provided on a connector portion 36 positioned in an accommodating part 34 to be described later. That is, the mixture electrode 38 is formed by applying mixture slurry on the connector portion 36 of the positive electrode collector 26 and then drying the applied mixture slurry. The mixture slurry is obtained by dispersing the positive electrode active material 38a, conductive assistant agent, and a binder (binding agent) in a solvent.

Preferably, in this positive electrode active material 38a, the average grain size of the secondary particles is preferably in a range between several μm and some dozen μm, and more preferably about 10 μm. The average grain size may be determined, e.g., by a section method. Further, the material suitable for forming the positive electrode active material 38a includes, for example, $LiCoO_2$, $LiMnO_2$, $LiMn_2O_4$, $LiNiO_2$, $LiFePO_4$, $Li_2FePO_4F$, $LiCo_{1/3}Ni_{1/3}Mn_{1/3}O_2$, or $Li(Li_\alpha Ni_x Mn_y Co_z)O_2$, etc.

For example, carbon black may be used as the conductive assistant agent, polyvinylidene difluoride (PVDF) may be used as the binder, and ethanol or the like may be used as the solvent. However, the present invention is not limited in this respect. The mixture electrode 38 may contain materials that are suitably selected depending on the type, etc. of the positive electrode active material 38a. Further, the mixture electrode 38 may additionally contain dispersing agent for preventing aggregation of the positive electrode active material 38a and dispersing the positive electrode active material 38a, and leveling agent for improving the wettability with electrolytic solution.

The negative electrode collector 24 and the positive electrode collector 26 including side walls thereof, but excluding the connector portions 30, 36 and exposed portions 42, 44, which protrude outside an overlapping portion 40 as described later, are covered with electrically insulating membranes 46. In this structure, the insulating membrane 46 avoids contact of the negative electrode collector 24 and the positive electrode collector 26 with an electrolytic solution 48 contained in the overlapping portion 40. Therefore, it is possible to suppress occurrence of side reactions, which are different from the electrode reactions in the negative electrode active material 32 and the mixture electrode 38, in the negative electrode collector 24 and the positive electrode collector 26. Consequently, it becomes possible to analyze only the electrode reactions as the analysis subjects, highly accurately.

Figure 4A:
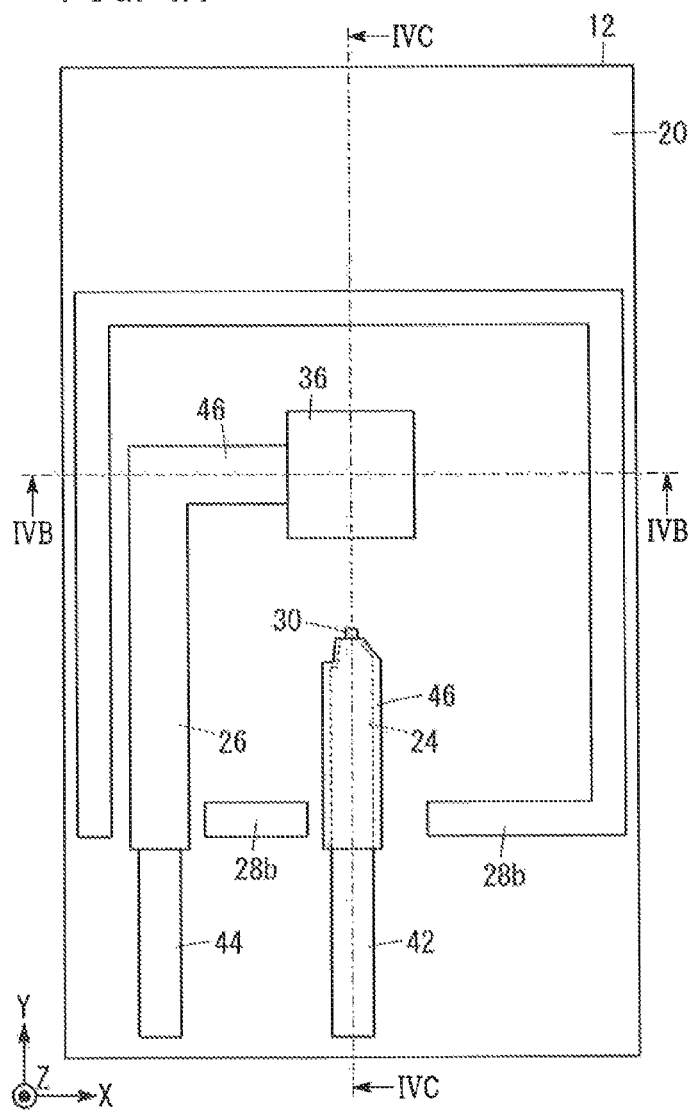
FIG. 4A is a plan view showing a state where an insulating membrane is provided on the negative electrode collector and the positive electrode collector in FIG. 3A, excluding exposed portions and connector portions thereof, and a second layer are provided on the first layer to form a joint portion.
Figure 4C:
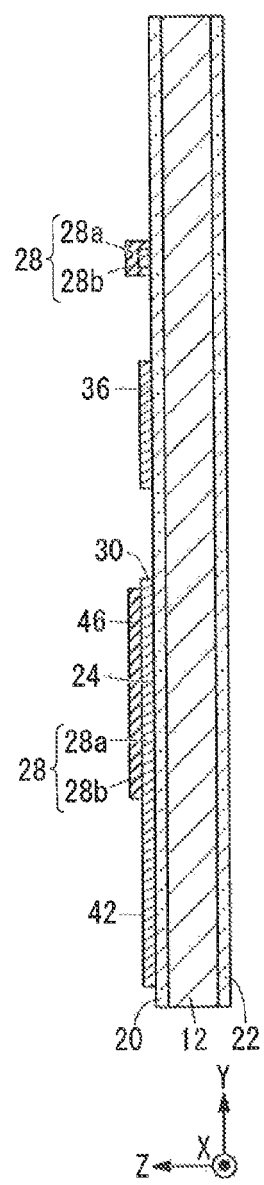
FIG. 4C is a sectional end view taken along a line IVC-IVC indicated by arrows in FIG. 4A.
Figure 6A:
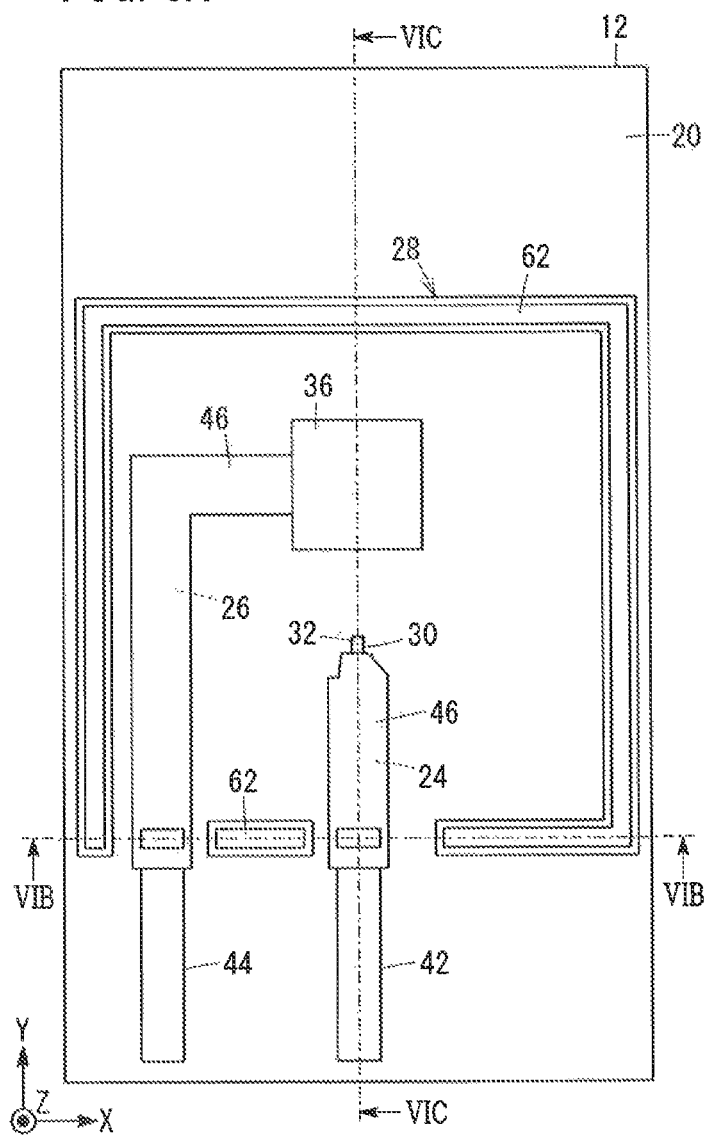
FIG. 6A is a plan view showing a state where a first solid portion is provided on the joint portion on the one surface of the first substrate in FIG. 5A.
Figure 6C:
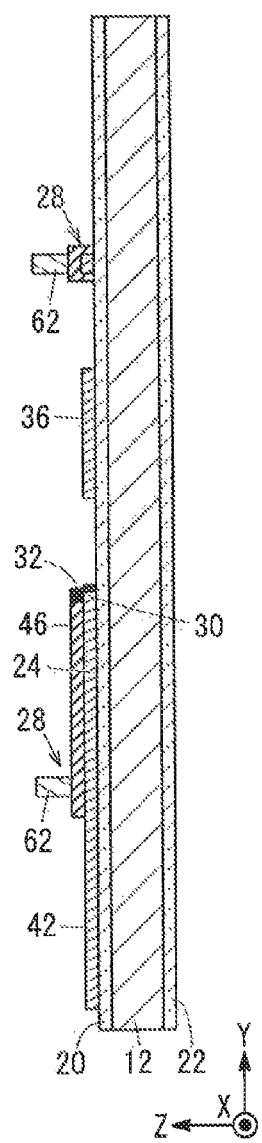
FIG. 6C is a sectional end view taken along a line VIC-VIC indicated by arrows in FIG. 6A.
Figure 6B:
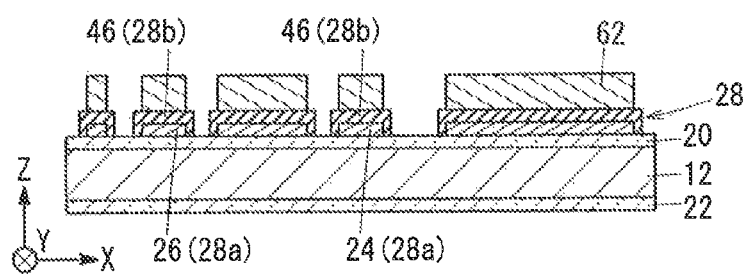
FIG. 6B is a sectional end view taken along a line VIB-VIB indicated by arrows in FIG. 6A.

The joint portion 28 is formed by stacking a first layer 28a and a second layer 28b together. The first layer 28a is made of the same material as the negative electrode collector 24 and the positive electrode collector 26. The second layer 28b is made of the same material as the insulating membrane 46. That is, as shown in FIGS. 4C and 6B, the negative electrode collector 24 and the positive electrode collector 26 partially have the function as the first layer 28a, and the insulating membrane 46 partially has the function of the second layer 28b. The side walls of the first layer 28a are covered with the second layer 28b.

The second substrate 14 is made of the same material as the first substrate 12. The width and the height of the second substrate 14 are substantially the same as the width and the height of the first substrate 12, and the depth of the second substrate 14 is smaller than the depth of the first substrate 12. A first through hole 50 is formed in the second substrate 14 at a position slightly shifted from the center in the depth direction toward the other end. The first through hole 50 extends through the second substrate 14 in the thickness direction. The first through hole 50 has a truncated square pyramid shape as in the case of the first through hole 18 of the first substrate 12. A second through hole 52 is formed in the second substrate 14 at a position slightly shifted from the center in the depth direction toward the one end. The second through hole 52 extends through the second substrate 14 in the thickness direction. Further, two injection ports 54 are formed in the second substrate 14 at positions adjacent to an end in the depth direction. The injection ports 54 extend through the second substrate 14 in the thickness direction.

Further, a transmission membrane 20 is provided on one surface of the second substrate 14 in a manner to cover the first through hole 50, and expose the second through hole 52 and the injection ports 54. A covering membrane 22 is provided on the other surface of the second substrate 14 in a manner to expose the first through hole 50, the second through hole 52 and the injection ports 54.

Though the width and the depth of the second through hole 52 are larger than the width and the depth of the first through holes 18, 50, the second through hole 52 has a truncated square pyramid shape as in the case of the first through holes 18, 50. Further, the second through hole 52 is closed with the lid member 16 and a seal member 56 from the other surface side of the second substrate 14.

For example, the lid member 16 is made of the same material as the first substrate 12 and the second substrate 14, and is a plate member having a size sufficient to close the second through hole 52. Both main surfaces of the lid member 16 are covered with the covering membranes 22. For example, the seal member 56 is made of epoxy resin, etc. The seal member 56 is formed on the other surface of the second substrate 14 along the outer circumferential edge of the lid member 16 to thereby function as a seal between the second through hole 52 and the lid member 16.

As described later, the injection ports 54 are formed for injecting the electrolytic solution 48 into the overlapping portion 40. After injection of the electrolytic solution 48, the injection ports 54 are closed by seal members 58 of epoxy resin, etc.

The first substrate 12 and the second substrate 14 are overlapped with each other such that one surface of the first substrate 12 and one surface of the second substrate 14 face each other across a solid state joint 60, whereby the overlapping portion 40 is formed. For example, the solid state joint 60 seals sides of the overlapping portion 40 except a side thereof extending in the width direction at the other end in the depth direction (hereinafter referred to as the wiring line side), i.e., seals three sides of the overlapping portion 40. The solid state joint 60 is formed continuously along the three sides, inward of the overlapping portion 40. Further, in the wiring line side, the solid state joint 60 is not formed adjacent to a transverse section extending across the wiring line side, in order for the negative electrode collector 24 and the positive electrode collector 26 to protrude from the inside to the outside of the overlapping portion 40. Stated otherwise, the solid state joint 60 is formed on an area of the wiring line side other than a portion adjacent to the transverse section. That is, the solid state joint 60 is formed on the transverse section as well (see FIG. 14A and FIG. 14B).

As described later, the solid state joint 60 is formed by solid state bonding of a first solid portion 62 (see FIGS. 7A to 7C) protruding on the joint portion 28 of the first substrate 12 and a second solid portion 64 (see FIGS. 9A and 9C) protruding on the transmission membrane 20 of the second substrate 14. That is, in the state where the first substrate 12 and the second substrate 14 are overlapped with each other, the first substrate 12 and the second substrate 14 are joined together by the solid state joint 60 to form the overlapping portion 40.

Further, in this overlapping portion 40, the first substrate 12 and the second substrate 14 are positioned such that the first through hole 18 of the first substrate 12 and the first through hole 50 of the second substrate 14 are disposed face-to-face with each other across the transmission membranes 20, and the second through hole 52 are disposed face-to-face with the connector portion 36 of the positive electrode collector 26. In the structure, an observation window 66 for allowing transmission of an electron beam through the transmission membranes 20 is formed between the first through holes 18, 50, and an accommodating part 34 is formed between the lid member 16 and the first substrate 12 through the second through hole 52.

Further, as described above, since the depth of the second substrate 14 is small in comparison with the depth of the first substrate 12, both ends of the first substrate 12 in the depth direction protrude out from the overlapping portion 40. The exposed portions 42, 44 of the negative electrode collector 24 and the positive electrode collector 26 are provided on a portion of the first substrate 12 that protrudes out from this overlapping portion 40.

The material suitable for the first solid portion 62 and the second solid portion 64 forming the solid state joint 60 includes a metal such as gold (Au), copper (Cu), or aluminum (Al), or an inorganic material such as $SiO_2$, Si. The material of the first solid portion 62 and the material of the second solid portion 64 may be the same, or may be different from each other. In the case where the first solid portion 62 and the second solid portion 64 are made of metal, as the solid state bonding, any of various methods, including hot pressure welding, cold pressure welding, diffusion welding, and friction pressure welding may be adopted. Further, in the case where the first solid portion 62 and the second solid portion 64 are made of inorganic material, for example, a bonding method by bringing the bonding surfaces activated by surface treatment into contact with each other may be adopted. In such a method, load does not necessarily have to be applied.

In the overlapping portion 40, for example, a seal member 68 of epoxy resin, etc. is provided in the area which is not sealed by the solid state joint 60 (area adjacent to the transverse section). In this structure, a liquid tight space is formed in the overlapping portion 40, and filled with the electrolytic solution 48. Therefore, in the analytical cell 10, it is not required to generate flow of the electrolytic solution 48 in the overlapping portion 40. Therefore, it is possible to reduce the pressure of the electrolytic solution 48 applied to the first substrate 12 and the second substrate 14. Accordingly, it is possible to reduce the distance between the substrates 12, 14, and reduce the overall size of the analytical cell 10.

As the electrolytic solution 48, for example, it is possible to suitably use solution obtained by adding supporting electrolyte such as lithium hexafluorophosphate ($LiPF_6$) of about 1M to propylene carbonate (PC), ethylene carbonate (EC), dimethyl carbonate (DMC), diethyl carbonate (DEC), ethyl methyl carbonate (EMC), vinylene carbonate (VC), etc.

The negative electrode active material 32 is provided between the transmission membranes 20 of the observation window 66 in a manner to contact the electrolytic solution 48. The transmission membranes 20 of this observation window 66 are kept spaced at a predetermined distance by the solid state joint 60 in correspondence with the height of the solid state joint 60. That is, by adjusting the height of the solid state joint 60, it is possible to adjust the thickness of the electrolytic solution layer of the observation window 66. Preferably, the thickness of the electrolytic solution layer of the observation window 66 is less than 5 μm, and more preferably, equal to or less than 2 μm.

The mixture electrode 38 containing the positive electrode active material 38a is provided on the connector portion 36 of the positive electrode collector 26 between the lid member 16 of the accommodating part 34 and the first substrate 12, in a manner to contact the electrolytic solution 48. In this manner, each of the negative electrode active material 32 and the mixture electrode 38 provided on the connector portions 30, 36 can be electrically connected to the outside of the overlapping portion 40 through the negative electrode collector 24 and the positive electrode collector 26. That is, the negative electrode collector 24 and the positive electrode collector 26 extend from the connector portions 30, 36 provided in the overlapping portion 40, and extend across the wiring line side. Thus, the negative electrode collector 24 and the positive electrode collector 26 are partially exposed to the outside of the overlapping portion 40, and form the exposed portions 42, 44.

The analytical cell 10 basically has the structure as described above. For example, in the TEM observation of the analytical cell 10, firstly, the analytical cell 10 is placed on the TEM holder (not shown) in such a manner that the observation window 66 faces an electron beam irradiation part of the TEM. Then, the exposed portions 42, 44 are electrically connected to the charge-discharge tester or the like, through an electrical path (not shown) provided in the holder to cause the electrode reactions as the observation subjects in the negative electrode active material 32 and the mixture electrode 38.

The analytical cell 10 may be produced by a known semiconductor process (see, e.g., International Publication No. WO 2008/141147). Hereinafter, a method of producing the analytical cell 10 according to the embodiment of the present invention will be described below with reference to FIGS. 2A to 16C. It is a matter of course that the method of producing the analytical cell 10, and the order of steps for production of the analytical cell 10 are not limited to those described in the following description. In this example, the first substrate 12, the second substrate 14, and the negative electrode active material 32 are made of silicon (Si), the positive electrode active material 38a contained in the mixture electrode 38 is made of lithium cobaltate ($LiCoO_2$), the transmission membrane 20 and the covering membrane 22 are made of silicon nitride ($Si_3N_4$), and the negative electrode collector 24 and the positive electrode collector 26 are made of tungsten (W).

As described above, the first solid portion 62 and the second solid portion 64 are provided separately and respectively on the first substrate 12 and the second substrate 14, and the first solid portion 62 and the second solid portion 64 are bonded together by solid state bonding to thereby form the overlapping portion 40, whereby the analytical cell 10 is obtained. Then, at the outset, steps of providing the constituent elements including the first solid portion 62 on the first substrate 12 will be described.

Figure 2C:
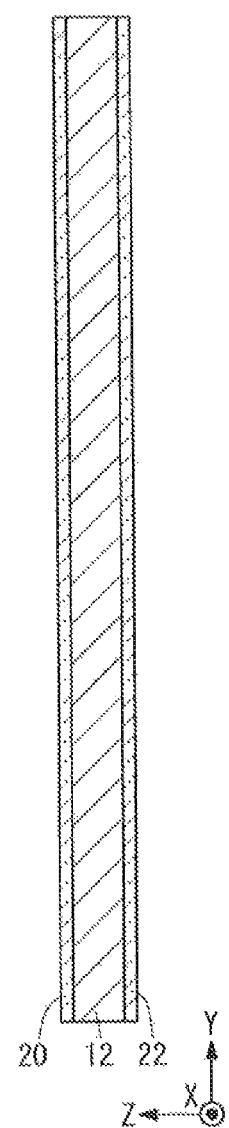
FIG. 2C is a cross sectional view taken along a line IIC-IIC indicated by arrows in FIG. 2A.
Figure 2B:
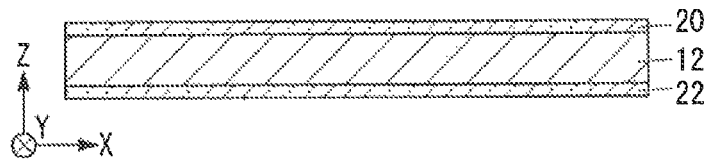
FIG. 2B is a cross sectional view taken along a line IIB-IIB indicated by arrows in FIG. 2A.

Firstly, as shown in FIGS. 2A to 2C, both surfaces of the first substrate 12 are polished, and each of the surfaces of the first substrate 12 is covered with a silicon nitride membrane by chemical vapor deposition (CVD). The silicon nitride membrane formed on the one surface of the first substrate 12 is used as the transmission membrane 20, and the silicon nitride membrane formed on the other surface is used as the covering membrane 22.

Next, the transmission membrane 20 of the first substrate 12 is covered with a photoresist (not shown), and a photolithography process is performed. In the photolithography process, the photoresist is removed only on portions where the negative electrode collector 24, the positive electrode collector 26, and the joint portion 28 should be formed. That is, in the process, only the portions where the negative electrode collector 24, the positive electrode collector 26, and the joint portion 28 should be formed are exposed.

Figure 3A:
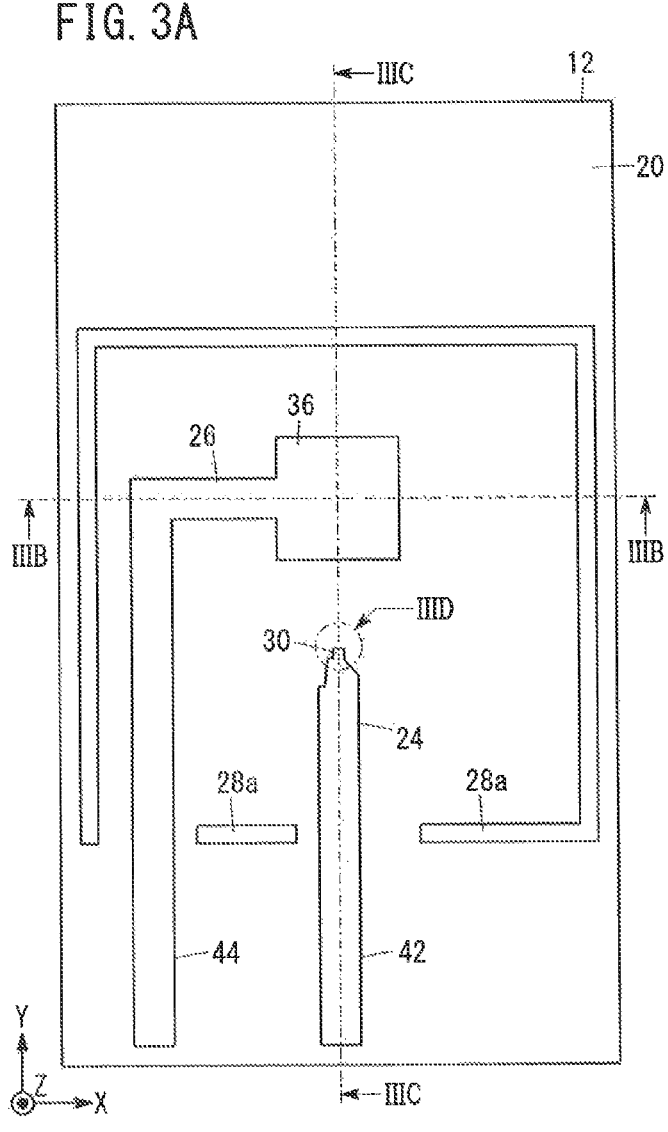
FIG. 3A is a plan view showing a state where a negative electrode collector, a positive electrode collector, and a first layer are provided on the one surface of the first substrate in FIG. 2A.
Figure 3C:
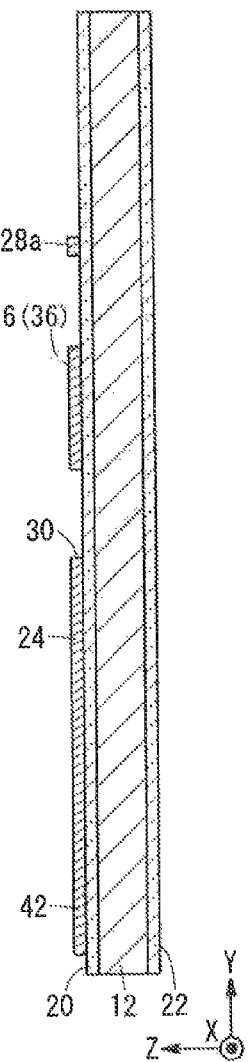
FIG. 3C is a sectional end view taken along a line IIIC-IIIC indicated by arrows in FIG. 3A.
Figure 3B:
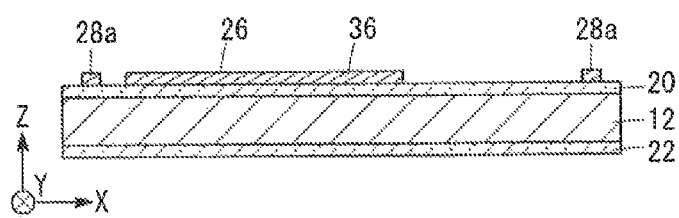
FIG. 3B is a sectional end view taken along a line IIIB-IIIB indicated by arrows in FIG. 3A.

Next, one surface of the first substrate 12 is covered with a tungsten membrane by radio frequency sputtering (RF sputtering), and thereafter, the entire photoresist is removed (by lift-off processing). As a result, as shown in FIGS. 3A to 3C, the negative electrode collector 24, the positive electrode collector 26, and the first layer 28a as the precursor of the joint portion 28, which are made up of the tungsten membranes, are formed on the transmission membrane 20 of the first substrate 12. At this time, the connector portion 30 of the negative electrode collector 24 has a shape shown in FIG. 3D.

Next, the one surface of the first substrate 12 is covered with a silicon nitride membrane by chemical vapor deposition (CVD). Then, this silicon nitride membrane is covered with a photoresist, and a photolithography process is performed. As a result of this process, the photoresist is left only on portions of the silicon nitride membrane that cover a portion of the negative electrode collector 24 excluding the connector portion 30 and the exposed portion 42, a portion of the positive electrode collector 26 excluding the connector portion 36 and the exposed portion 44, and all of the first layer 28a. It should be noted that the photoresist is also left on portions of the silicon nitride membrane that cover the side walls of the above portions of the negative electrode collector 24 and the positive electrode collector 26, and the side wall of the first layer 28a.

Figure 4B:
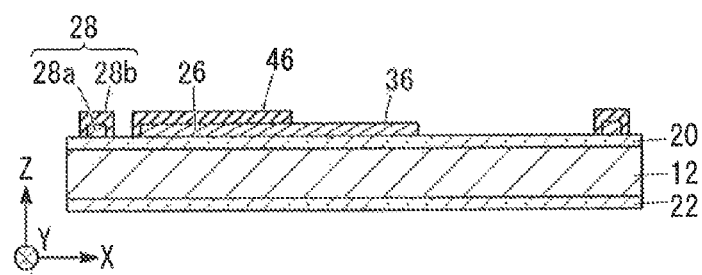
FIG. 4B is a sectional end view taken along a line IVB-IVB indicated by arrows in FIG. 4A.

Next, for example, a dry etching process such as a reactive ion etching process is carried out using the photoresist as a mask. In this process, the silicon nitride membrane covered with the residual photoresist as described above are protected. Thereafter, the entire photoresist is removed. Consequently, as shown in FIGS. 4A to 4C, the silicon nitride membrane covering the portion of the negative electrode collector 24 excluding the connector portion 30 and the exposed portion 42, the portion of the positive electrode collector 26 excluding the connector portion 36 and the exposed portion 44, and the first layer 28a is formed. It is a matter of course that the side walls of the above portions of the negative electrode collector 24 and the positive electrode collector 26, and the side wall of the first layer 28a are also covered with the silicon nitride membrane.

The part of the silicon nitride membrane covering the negative electrode collector 24 and the positive electrode collector 26 forms the insulating membrane 46, and the other part of the silicon nitride membrane covering the first layer 28a forms the second layer 28b. That is, the first layer 28a and the second layer 28b form the joint portion 28.

Next, the one surface of the first substrate 12 is covered with a photoresist, and a photolithography process is performed. In the photolithography process, the photoresist on a portion where the negative electrode active material 32 should be formed is removed. As a result, only the portion of the connector portion 30 of the negative electrode collector 24 where the negative electrode active material 32 should be formed is exposed.

Next, the one surface of the first substrate 12 is covered with a silicon membrane by radio frequency sputtering (RF sputtering), and thereafter, the photoresist is completely removed. As a result, as shown in FIGS. 5A to 5D, the negative electrode active material 32 made up of a silicon membrane is formed on the connector portion 30 of the negative electrode collector 24.

Then, the one surface of the first substrate 12 is covered with a photoresist, and a photolithography process is performed. In the photolithography process, the photoresist on a portion where the first solid portion 62 should be formed is removed. As a result, only the joint portion 28 and the transverse sections of the negative electrode collector 24 and the positive electrode collector 26 are exposed. In this regard, the thickness of photoresist should be determined to have a value that is about twice to 10 times as large as a desired length by which the first solid portion 62 protrudes.

Next, using the PVD method, the one surface of the first substrate 12 is covered with a chromium membrane, and then, covered with a gold membrane. At the time of forming the membranes, using a membrane quantity measuring instrument as an accessory device of the PVD apparatus, in-situ monitoring of the membrane quantity (thickness) is conducted, and the deposited membrane thickness is controlled. In this manner, the membrane thickness control in the order of several nanometers can be performed. Thereafter, the entire photoresist is removed. Consequently, as shown in FIGS. 6A to 6C, the first solid portion 62 as a stack body of the chromium membrane and the gold membrane is formed on the transmission membrane 20 of the first substrate 12.

Next, the covering membrane 22 on the other surface of the first substrate 12 is covered with a photoresist, and a photolithography process is performed. As a result, the photoresist is removed to expose part of the covering membrane 22 provided on a portion where the first through hole 18 should be formed in the first substrate 12.

Next, a dry etching process is carried out using the photoresist as a mask. As a result, only the part of the covering membrane 22 exposed from the photoresist is removed from the first substrate 12. In this manner, after removing the part of the covering membrane 22 provided on the portion of the first substrate 12 where the first through hole 18 should be formed in the first substrate 12, the entire photoresist is removed.

Figure 7B:
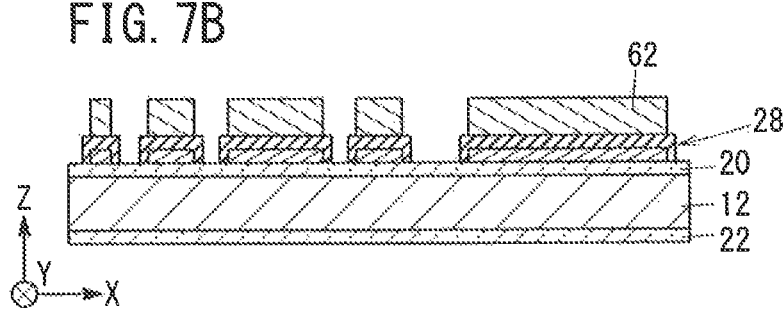
FIG. 7B is a sectional end view taken along a line VIIB-VIIB indicated by arrows in FIG. 7A.

Next, as shown in FIGS. 7A to 7C, a wet etching process (through hole etching) is applied to the other surface of the first substrate 12 to thereby form the first through hole 18. In this manner, the first through hole 18 is formed in the first substrate 12. The first through hole 18 is covered with the transmission membrane 20, from the one surface side of the first substrate 12. The one surface of the first substrate 12 may be covered with an alkali-resistant surface protection layer (not shown) before performing the wet etching process. In this case, the one surface of the first substrate 12 can be protected by the alkali-resistant surface protection layer. Further, the alkali-resistant surface protection layer should be removed by dry etching or removing liquid after forming the first through hole 18 as described above.

Figure 8A:
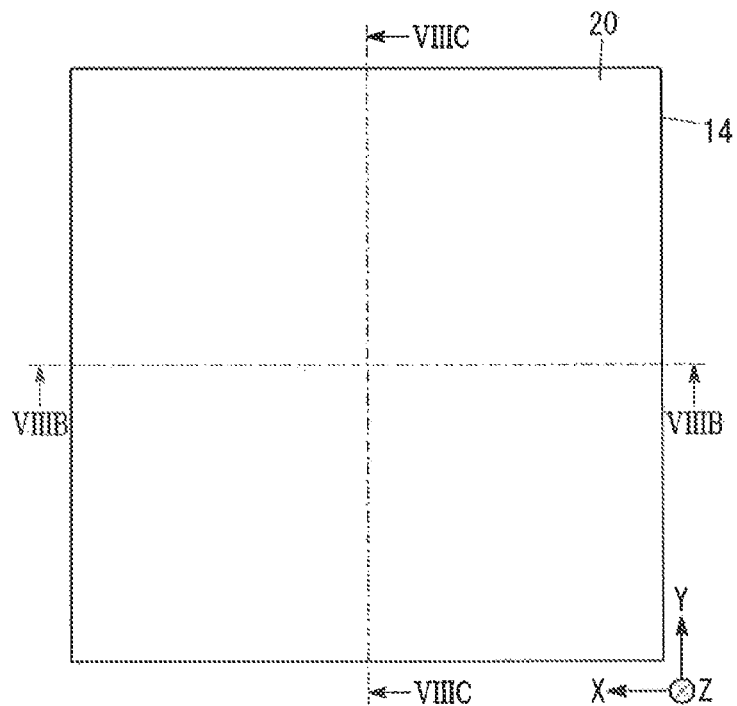
FIG. 8A is a plan view showing a transmission membrane of a second substrate having the transmission membrane on one surface and a covering membrane on the other surface.
Figure 8C:
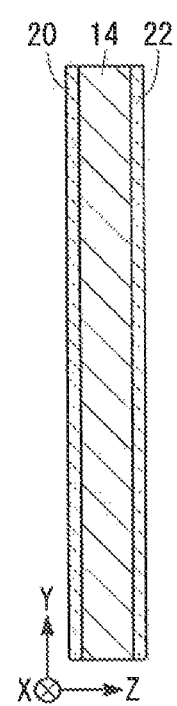
FIG. 8C is a cross sectional view taken along a line VIIIC-VIIIC indicated by arrows in FIG. 8A.
Figure 8B:
FIG. 8B is a cross sectional view taken along a line VIIIB-VIIIB indicated by arrows in FIG. 8A.

Also on the second substrate 14, as shown in FIGS. 8A to 8C, in the same manner as in the case of the first substrate 12, the transmission membrane 20 and the covering membrane 22 are provided. Next, the one surface of the second substrate 14 is covered with a photoresist, and a photolithography process is performed. As a result, the photoresist on a portion where the second solid portion 64 should be formed is removed. Thus, of the transmission membrane 20 on the second substrate 14, only a portion along the four sides of the overlapping portion 40, inside the overlapping portion 40 is exposed. In this regard, the thickness of the photoresist should be determined to have a value that is about twice to 10 times as large as a desired length by which the second solid portion 64 protrudes.

Figure 9A:
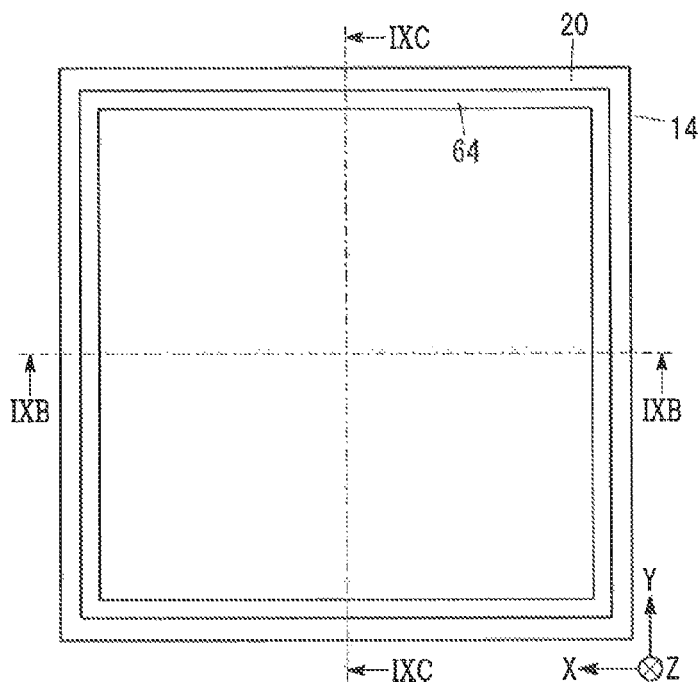
FIG. 9A is a plan view showing a state where a second solid portion is provided on the one surface of the second substrate in FIG. 8A.
Figure 9C:
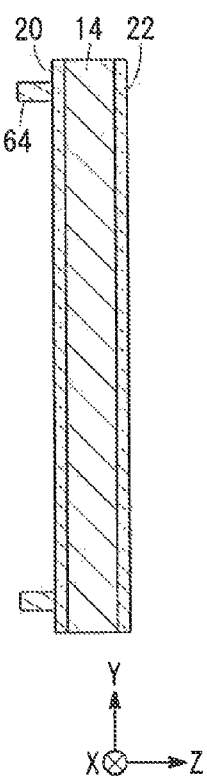
FIG. 9C is a sectional end view taken along a line IXC-IXC indicated by arrows in FIG. 9A.
Figure 9B:
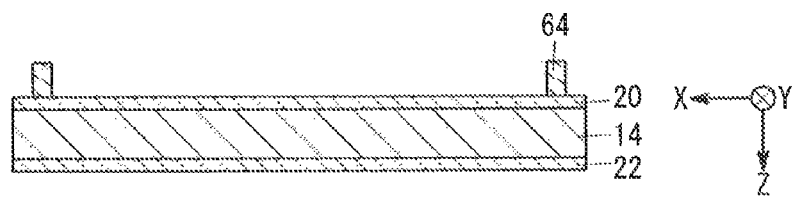
FIG. 9B is a sectional end view taken along a line IXB-IXB indicated by arrows in FIG. 9A.

Next, using the PVD method, the one surface of the second substrate 14 is covered with a chromium membrane, and then, covered with a gold membrane. At the time of forming the membranes, using a membrane quantity measuring instrument as an accessory device of the PVD apparatus, in-situ monitoring of the membrane quantity (thickness) is conducted, and the deposited membrane thickness is controlled. In this manner, the membrane thickness control in the order of several nanometers can be performed. Thereafter, the entire photoresist is removed. Consequently, as shown in FIGS. 9A to 9C, the second solid portion 64 as a stack body of the chromium membrane and the gold membrane is formed on the transmission membrane 20 of the second substrate 14.

Next, the one surface of the second substrate 14 is covered with a photoresist, and a photolithography process is performed. As a result, the photoresist is partly removed so as to expose part of the transmission membrane 20 provided on portions where the second through hole 52 and the injection ports 54 should be formed in the second substrate 14.

Figure 10A:
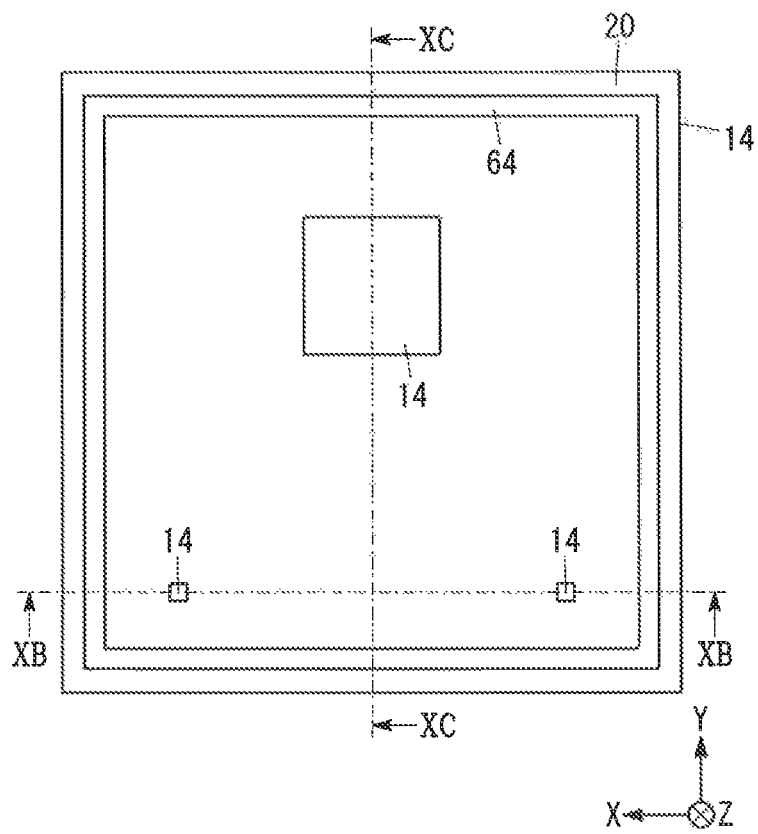
FIG. 10A is a plan view showing a state where part of the transmission membrane on the second substrate in FIG. 9A that corresponds to a portion for forming a second through hole and portions for forming injection ports has been removed.
Figure 10C:
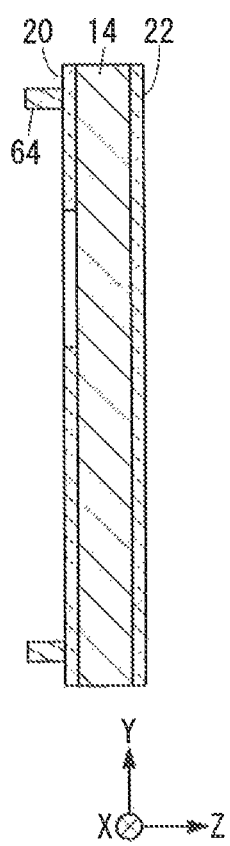
FIG. 10C is a sectional end view taken along a line XC-XC indicated by arrows in FIG. 10A.
Figure 10B:
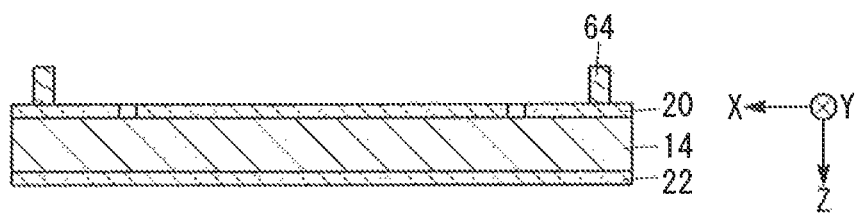
FIG. 10B is a sectional end view taken along a line XB-XB indicated by arrows in FIG. 10A.

Next, a dry etching process is carried out using the photoresist as a mask. As a result, only the part of the transmission membrane 20 provided on the portions where the second through hole 52 and the injection ports 54 should be formed is removed. Thereafter, the entire photoresist is removed. In this manner, as shown in FIGS. 10A to 10C, only the part of the transmission membrane 20 provided on the portions of the second substrate 14 where the second through hole 52 and the injection ports 54 should be formed is removed, and the portions of the second substrate 14 are exposed.

Next, the covering membrane 22 on the other surface of the second substrate 14 is covered with a photoresist, and a photolithography process is performed. As a result, the photoresist is partly removed to expose part of the covering membrane 22 provided on portions where the first through hole 50, the second through hole 52, and the injection ports 54 should be formed in the second substrate 14.

Next, a dry etching process is carried out using the photoresist as a mask. As a result, only the part of the covering membrane 22 provided on the portions where the first through hole 50, the second through hole 52, and the injection ports 54 should be formed is removed. Thereafter, the entire photoresist is removed. In this manner, as shown in FIGS. 11A to 11C, only the part of the covering membrane 22 provided on the portions of the second substrate 14 where the first through hole 50, the second through hole 52, and the injection ports 54 should be formed is removed, and the portions of the second substrate 14 are exposed.

Figure 12A:
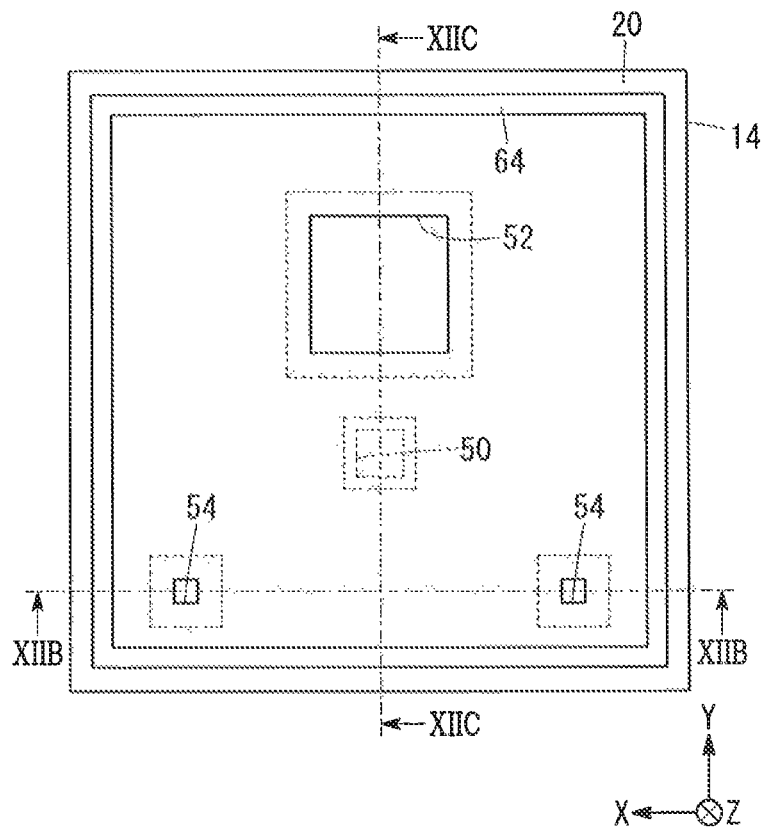
FIG. 12A is a plan view showing a state where the first through hole, the second through hole, and the injection ports are formed in the second substrate in FIG. 11A.
Figure 12C:
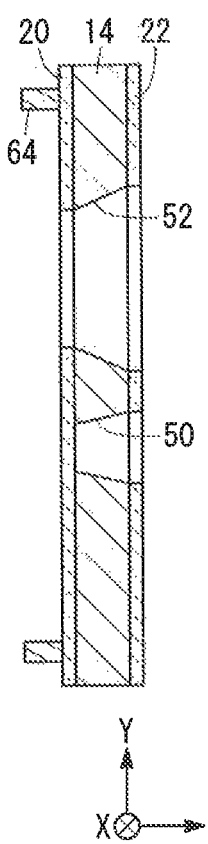
FIG. 12C is a sectional end view taken along a line XIIC-XIIC indicated by arrows in FIG. 12A.
Figure 12B:
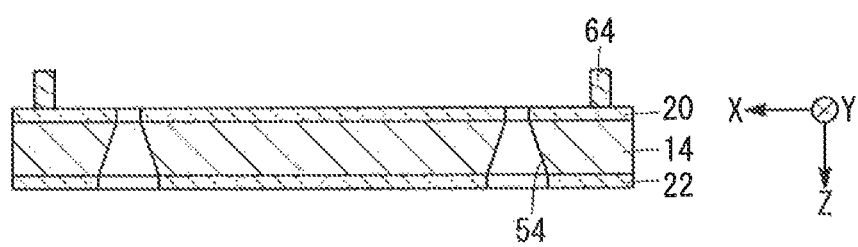
FIG. 12B is a sectional end view taken along a line XIIB-XIIB indicated by arrows in FIG. 12A.

Next, as shown in FIGS. 12A to 12C, a wet etching process (through hole etching) is applied to the second substrate 14 to thereby form the first through hole 50, the second through hole 52, and the injection ports 54. As a result, the first through hole 50 covered with the transmission membrane 20, from the one surface side of the second substrate 14 is formed in the second substrate 14, and the second through hole 52 and the injection ports 54 exposed from the transmission membrane 20 and the covering membrane 22 are formed in the second substrate 14.

After the above series of processes, the first substrate 12 and the second substrate 14 having the various constituent components are overlapped with each other, and the first solid portion 62 and the second solid portion 64 are brought into contact with each other. At this time, for example, an adjustment is made in a manner that the edge of the first through hole 18 formed in the first substrate 12 and the edge of the first through hole 50 formed in the second substrate 14 are overlapped and in alignment with each other in a plan view. Thus, positioning can be performed easily and highly accurately in a manner that the observation window 66 is formed by the first through holes 18, 50 facing each other across the transmission membranes 20, and the second through hole 52 faces the connector portion 36 of the positive electrode collector 26.

In order to suppress variation in the contact area between the first solid portion 62 and the second solid portion 64 that are placed in contact with each other as described above, preferably, the protruding end surfaces (joint end surfaces) of the first solid portion 62 and the second solid portion 64 have different lengths in the lateral direction. In the structure, when a load is applied to the first solid portion 62 and the second solid portion 64 so as to be placed in contact as described later, it is possible to suppress the occurrence of pressure variation, and improve the bonding uniformity by the solid state joint 60.

In the embodiment where the contact surfaces of the first solid portion 62 and the second solid portion 64 are made of gold, as described above, the bonding surface of the first solid portion 62 and the bonding surface of the second solid portion 64 are brought into abutment against each other. In this state, a pressure load in a range of 0.2 to 2.0 kgf, preferably 1.0 kgf, per the unit bonding area of 1 mm$^2$ may be applied to the first solid portion 62 and the second solid portion 64, e.g., at temperature in a range of 300 to 400° C., preferably at temperature of 300° C. for 15 to 60 minutes. In this manner, solid state bonding of the first solid portion 62 and the second solid portion 64 is performed firmly to thereby obtain the solid state joint 60.

In the case where the first solid portion 62 and the second solid portion 64 are made of aluminum, the same load as described above should be applied at temperature in a range of 400 to 450° C., preferably at temperature of 400° C., for the same time period as described above. Alternatively, in the case where the first solid portion 62 and the second solid portion 64 are made of copper, the same load as described above should be applied at temperature in a range of 350 to 450° C., preferably at temperature of 350° C., for the same time period as described above.

Further, in the case where the first solid portion 62 and the second solid portion 64 are made of the above-described inorganic material, the bonding surfaces of the first solid portion 62 and the second solid portion 64 should be activated before formation of the overlapping portion 40. Activation of such boding surfaces can be performed using existing devices such as a room-temperature wafer bonder "BOND MEISTER" (product name) of Mitsubishi Heavy Industries, Ltd., a surface activation wafer bonding kit (Model type: WP-100) of PMT Corporation, or the like.

More specifically, sputter etching using ion beams, plasma, etc. may be applied to each of the bonding surfaces in a vacuum chamber at room temperature under high vacuum. In this manner, it is possible to remove an oxide film and absorption films comprising water, organic material, etc., formed on the bonding surfaces to thereby expose atoms having bonds, i.e., activate the bonding surfaces. If the bonding surfaces activated in this manner are brought into contact with each other, since a bonding force is generated between the bonding surfaces, it is possible to obtain the solid state joint 60 formed by firm solid state bonding of the first solid portion 62 and the second solid portion 64. The bonding conditions in this process should be determined appropriately based on the material, shape, or the like of the first solid portion 62 and the second solid portion 64.

Figure 13A:
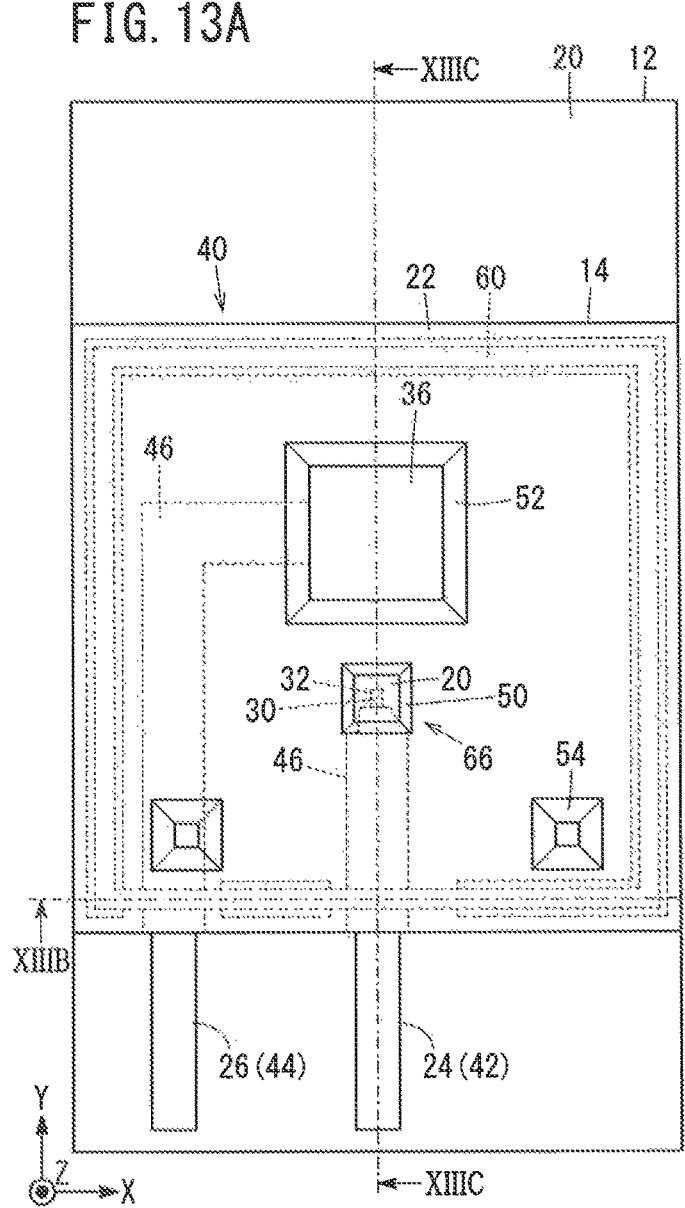
FIG. 13A is a plan view showing a state where the first solid portion of the first substrate in FIG. 7A and the second solid portion of the second substrate in FIG. 12A are solid-state bonded together to form a solid state joint and thereby form an overlapping portion.
Figure 13C:
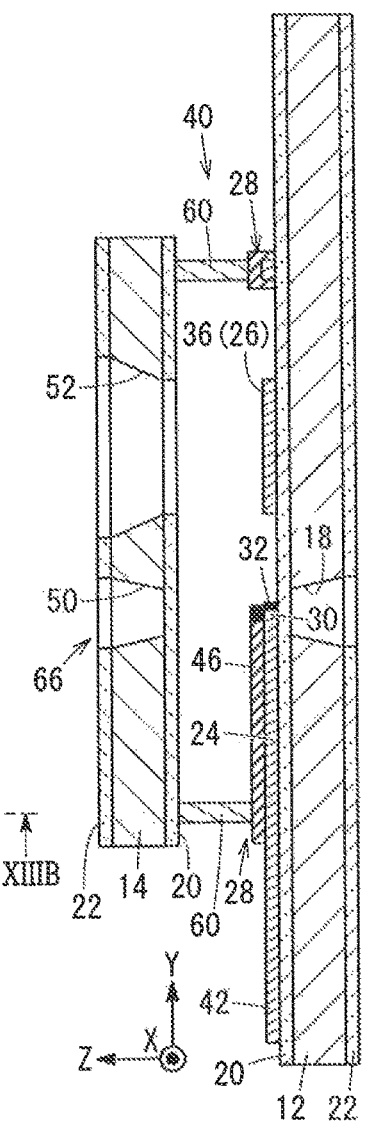
FIG. 13C is a sectional end view taken along a line XIIIC-XIIIC indicated by arrows in FIG. 13A.
Figure 13B:
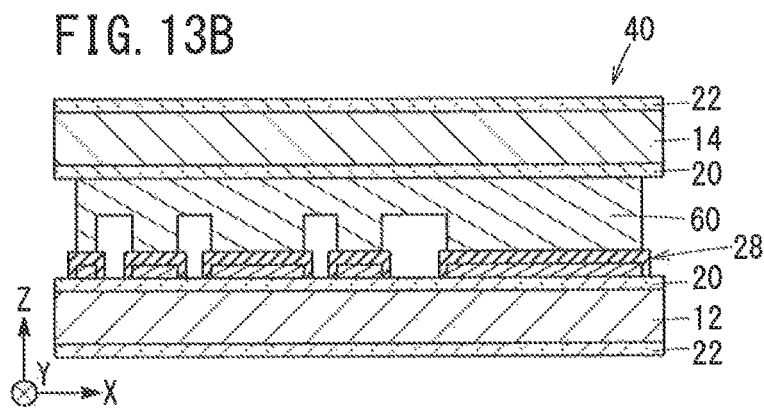
FIG. 13B is a sectional end view taken along a line XIIIB-XIIIB indicated by arrows in FIG. 13A.

By forming the solid state joint 60 by the above solid state bonding, as shown in FIGS. 13A to 13C, the first substrate 12 and the second substrate 14 are joined together in the state where the overlapping portion 40 is formed, and the transmission membranes 20 of the first substrate 12 and the second substrate 14 are kept spaced from each other by a distance in correspondence with the height of the solid state joint 60. This solid state joint 60 is formed without melting the first solid portion 62 and the second solid portion 64. Therefore, the height of the solid state joint 60 becomes substantially equal to the sum of the heights of the first solid portion 62 and the second solid portion 64. That is, by adjusting the height of the first solid portion 62 and the height of the second solid portion 64, it is possible to make settings of the distance between the transmission membrane 20 of the first substrate 12 and the transmission membrane 20 of the second substrate 14 easily.

Then, as shown in FIGS. 14A to 14C, the seal members 68 are provided adjacent to the transverse sections on the first substrate 12. As described above, by providing the seal members 68 only in portions that are not sealed by the solid state joint 60, the outer circumference of the overlapping portion 40 can be sealed. Therefore, it is possible to simplify the production processes and reduce the production cost of the analytical cell 10.

Next, as shown in FIGS. 15A to 15C, the mixture electrode 38 containing the positive electrode active material 38a in the form of particles is provided on the connector portion 36 of the positive electrode collector 26. Specifically, firstly, the positive electrode active material 38a (LiCoO$_2$), a binding agent, and a conductive assistant agent are dispersed into a solvent to prepare mixture slurry.

The mixture slurry prepared in this manner is placed on the connector portion 36 of the positive electrode collector 26 through the second through hole 52. Thereafter, a drying process is performed to remove the solvent in the mixture slurry. Thus, the mixture electrode 38 is obtained.

Next, as shown in FIGS. 16A to 16C, the lid member 16 with the covering membranes 22 formed on both main surfaces thereof is fixed to the other surface of the second substrate 14 using the seal member 56 to thereby close the second through hole 52. Thus, the accommodating part 34 is formed in the state where the mixture electrode 38 is accommodated between the lid member 16 and the first substrate 12 through the second through hole 52.

Next, the electrolytic solution 48 is injected from the injection ports 54 into the overlapping portion 40. In the state where the space in the overlapping portion 40 is filled with the electrolytic solution 48, the injection ports 54 are closed by the seal members 56. As a result, the negative electrode active material 32 provided between the transmission membranes 20 of the observation window 66, and the mixture electrode 38 provided in the accommodating part 34 separately contact the electrolytic solution 48 in the overlapping portion 40, to thereby form the lithium ion cell. That is, it is possible to obtain the analytical cell 10.

The height of the accommodating part 34 of this analytical cell 10 is the distance from the first substrate 12 to the lid member 16 through the second through hole 52. Thus, the height of the accommodating part 34 can be increased without increasing the distance between the transmission membranes 20 of the observation window 66 (i.e., thickness of the electrolytic solution layer of the observation window 66). Accordingly, the mixture electrode 38 containing the granular positive electrode active material 38a having the grain size larger than the thickness of the electrolytic solution layer of the observation window 66 can be placed in the accommodating part 34. That is, in this analytical cell 10, the reaction conditions can be made closer to the actual reaction conditions of the practical cell without degrading the resolution of the observation result.

Further, since the first substrate 12 and the second substrate 14 are jointed together by the solid state joint 60, the height of the solid state joint 60 becomes substantially equal to the thickness of the electrolytic solution layer of the observation window 66. Further, the height of the solid state joint 60 becomes substantially equal to the sum of the protruding lengths of the first solid portion 62 and the second solid portion 64. Therefore, by adjusting the sum of the above protruding lengths, it is possible to make settings of the thickness of the electrolytic solution layer of the observation window 66 easily and highly accurately. Accordingly, for example, it is possible to make settings of the thickness of the electrolytic solution layer easily and highly accurately so as to obtain the observation result at the high resolution.

As described above, in the analytical cell 10 according to the invention, without increasing the thickness of the electrolytic solution layer of the observation window 66, the mixture electrode 38 containing the positive electrode active material 38a having the grain size which is larger than the thickness of the electrolytic solution layer of the observation window 66 can be placed in the accommodating part 34. Further, by joining the first substrate 12 and the second substrate 14 together using the solid state joint 60, it is possible to easily and highly accurately adjust the thickness of the electrolytic solution layer of the observation window 66 to have a desired value. As a result, it is possible to obtain highly-accurate observation results under reaction conditions close to the actual reaction conditions of the practical cell. Further, it is possible to firmly join the first substrate 12 and the second substrate 14 together by the solid state joint 60. Accordingly, even in the case where the analytical cell 10 is attached to the holder, or an electron microscope observation is performed under high vacuum, it is possible to suppress positional displacement between the first substrate 12 and the second substrate 14 and occurrence of changes in the thickness of the electrolytic solution layer.

The present invention is not limited to the embodiments described above, and various modifications can be made without deviating from the scope of the present invention.

For example, the analytical cell 10 according to the above embodiment includes the negative electrode active material 32 in the form of a layered structure and the mixture electrode 38 containing the positive electrode active material 38a in the form of particles. However, the present invention is not limited to the above. That is, the analytical cell 10 may include a mixture electrode containing the negative electrode active material in the form of particles and a positive electrode active material in the form of a layered structure. In this case, the positive electrode active material in the form of a layered structure is placed between the transmission membranes 20 of the observation window 66, and the mixture electrode containing the negative electrode active material in the form of particles is placed in the accommodating part 34, whereby the working effects and advantages as described above can be obtained.

Furthermore, in the case where the analytical cell 10 or the like of the above embodiment is not the lithium-ion secondary cell but the nickel-hydrogen cell, for example, a positive electrode of nickel hydroxide, a negative electrode of any of various hydrogen storing alloys, and an electrolytic solution of an aqueous potassium hydroxide solution KOH (aq) may be used. Alternatively, in the case where the analytical cell 10 is the alkaline-manganese cell, for example, a positive electrode of manganese dioxide/graphite, a negative electrode of zinc, and an electrolytic solution of KOH(aq) may be used.

Further, the analytical cell 10 can be used in an analysis not only in the TEM but also in any general analytical equipment using an electron beam.

EMBODIMENT EXAMPLE

Using the above steps, the analytical cell 10 according to the embodiment example was produced. Specifically, as the first substrate 12, a silicon substrate having the width of 4.0 mm, the depth of 7.0 mm, and the thickness of 200 µm was adopted. A first through hole 18 having the width of 60 µm and the depth of 60 µm was formed in the silicon substrate. Further, as the transmission membrane 20, a silicon nitride membrane having the thickness of 80 nm was adopted. As the negative electrode collector 24 and the positive electrode collector 26, tungsten membranes having the thickness of 120 nm were adopted.

Figure 3D:
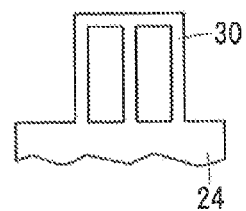
FIG. 3D is an enlarged view showing the negative electrode collector and an area around the negative electrode collector, indicated by an arrow IIID in FIG. 3A.

The connector portion 30 of the negative electrode collector 24 had a shape shown in FIG. 3D. Further, the width and the depth of the connector portion 36 of the positive electrode collector 26 were 900 µm. As the negative electrode active material 32, silicon having a shape shown in FIG. 5D was adopted. As the insulating membrane 46, a silicon nitride membrane having the thickness of 160 nm was adopted.

The joint portion 28 was formed by covering a first layer 28a (thickness of 120 nm) with a second layer 28b (thickness of 160 nm). The first layer 28a comprises a tungsten membrane formed in the same manner as the negative electrode collector 24 and the positive electrode collector 26. The second layer 28b comprises a silicon nitride membrane formed in the same manner as the insulating membrane 46. That is, the thickness of the joint portion 28 was 280 nm.

The first solid portion 62 was a stack body including a chromium membrane formed on the joint portion 28 and a gold membrane formed on the chromium membrane. The thickness of this chromium membrane was 50 nm, and the thickness of the gold membrane was 200 nm. Therefore, the protruding length of the first solid portion 62 was 250 nm. Each of the sides of the first solid portion 62 in the depth direction and in the width direction had the length of 3.75 mm. The length of the protruding end surface of the first solid portion 62 in the lateral direction had the length of 0.1 mm. That is, the surface area of the protruding end surface of the first solid portion 62 was 1.235 $mm^2$.

Further, as the second substrate 14, a silicon substrate having the width of 4.0 mm, the depth of 4.0 mm, and the thickness of 200 µm was adopted. A first through hole 50 having the same shape as the first through hole 18 of the first substrate 12, a second through hole 52 having the width of 1100 μm and the depth of 1100 μm, and injection ports 54 each having the width of 500 μm and the depth of 500 μm were formed in the silicon substrate. The second solid portion 64 was a stack body including a chromium membrane formed on the transmission membrane 20 and a gold membrane formed on the chromium membrane. The thickness of this chromium membrane was 50 nm, and the thickness of the gold membrane was 400 nm. Therefore, the protruding length of the second solid portion 64 was 450 nm. Each of the sides of the second solid portion 64 in the depth direction and in the width direction had the length of 3.8 mm. The length of the protruding end surface of the second solid portion 64 in the lateral direction had the length of 0.15 mm. That is, the surface area of the protruding end surface of the second solid portion 64 was 2.2 mm².

Therefore, the bonding area for bonding the first solid portion 62 and the second solid portion 64 by solid state bonding was 1.235 mm². Further, since the total value of the protruding lengths of the first solid portion 62 and the second solid portion 64 was 700 nm, the preset value of the height of the solid state joint 60 was 700 nm. That is, in the analytical cell 10 according to the embodiment example, 980 nm, which was the total value of the heights of the solid state joint 60 and the joint portion 28, was used as a target setting value of the distance between the transmission membranes 20 of the first substrate 12 and the second substrate 14.

Then, the first substrate 12 and the second substrate 14 were overlapped with each other and positioned as described above, so that the protruding end surfaces of the first solid portion 62 and the second solid portion 64 were brought into abutment against (contact with) each other. In such a state, solid state bonding was performed by applying a load of 1000 g at 350° C. for 30 minutes. That is, a load of 0.81 kgf per the bonding area of 1 mm² was applied to form the solid state joint 60, whereby the first substrate 12 and the second substrate 14 were joined together to thereby form the overlapping portion 40. In this overlapping portion 40, it was confirmed that the distance between the transmission membranes 20 of the first substrate 12 and the second substrate 14 was substantially 1000 nm. That is, as a result of obtaining the overlapping portion 40 as described above, the distance between the transmission membranes 20 of the first substrate 12 and the second substrate 14, i.e., the thickness of the electrolytic solution layer of the observation window 66, had substantially the target setting value.

In order to seal the areas adjacent to the transverse sections of the overlapping portion 40, seal members 68 of epoxy resin were provided. Thereafter, mixture slurry for providing the mixture electrode 38 in the overlapping portion 40 was prepared as follows: Specifically, ethanol was used as solvent, and lithium cobalt oxide (LiCoO₂) where the average grain size of secondary particles was about 10 μm was used as the positive electrode active material 38a, PVDF was used as a binding agent, and carbon black was used as a conductive assistant agent. Then, the active material of 0.08 g, the binder of 0.01 g, and the conductive assistant agent of 0.01 g were dispersed into the solvent of 5 g to obtain the mixture slurry.

This mixture slurry was adhered to a wire by surface tension, and the wire with the mixture slurry was inserted into the overlapping portion 40 through the second through hole 52 to dispose the mixture slurry on the connector portion 36 of the positive electrode collector 26 through the wire. Thereafter, the mixture slurry was dried at 60° C. for one hour to thereby obtain the mixture electrode 38 containing the granular positive electrode active material 38a.

Then, the lid member 16 was placed on the other surface of the second substrate 14, and the circumferential edge portion of the lid member 16 is sealed by the seal member 56 of epoxy resin to close the second through hole 52. As the lid member 16, a silicon substrate was adopted. The silicon substrate had the thickness of 200 μm. Both main surfaces of the silicon substrate were each covered with a covering membrane 22 comprising a silicon nitride membrane having the thickness of 80 nm.

Next, the electrolytic solution 48 was prepared by dissolving LiPF₆, at the concentration of 1M, in a solution obtained by mixing EC and EMC at the ratios of 3:7. The resulting electrolytic solution 48 was injected into the overlapping portion 40 through the injection ports 54. Thereafter, the injection ports 54 were closed by the seal members 58 of epoxy resin. As a result, in the overlapping portion 40, the negative electrode active material 32 and the mixture electrode 38 separately contact the electrolytic solution 48, to thereby produce the analytical cell 10 according to the embodiment example. The analytical cell 10 is a lithium ion cell.

In this analytical cell 10, the thickness of the electrolytic solution layer of the observation window 66 had 1 μm which was substantially equal to the target setting value. Accordingly, it was possible to obtain TEM observation images having the suitable resolution. Further, in this analytical cell 10, it was possible to provide, in the overlapping portion 40, the mixture electrode 38 that contained the positive electrode active material 38a having the average grain size of the secondary particles which is about 10 times as large as the thickness of the electrolytic solution layer of the observation window 66. Therefore, it was possible to perform observation of the analytical cell 10 under reaction conditions close to the actual reaction conditions of the practical cell. Further, the first substrate 12 and the second substrate 14 were joined together firmly through the solid state joint 60. Thus, it was confirmed that the state where the first substrate 12 and the second substrate 14 were positioned in the manner as described above was maintained suitably.

What is claimed is:

1. An analytical cell comprising a first substrate and a second substrate overlapped with each other to form an overlapping portion, a negative electrode active material and a positive electrode active material being provided in the overlapping portion and separately contacting electrolytic solution, an observation window for transmission of an electron beam being formed in the overlapping portion, wherein the first substrate and the second substrate have respective first through holes extending therethrough in a thickness direction thereof;

the second substrate further has a second through hole extending therethrough in the thickness direction;

the first through holes are covered with respective transmission membranes respectively from one surface side of the first substrate and one surface side of the second substrate, the transmission membranes each having an electron beam permeability;

the second through hole is closed by a lid member from another surface side of the second substrate, in the overlapping portion, the first substrate and the second substrate are joined together by a solid state joint, and the transmission membrane of the first substrate and the transmission membrane of the second substrate are spaced from each other by a predetermined distance, the solid state joint being formed by solid state bonding of a first solid portion protruding from the first substrate and a second solid portion protruding from the second substrate;

the first substrate and the second substrate are positioned to each other, wherein the observation window is formed at a position where the first through holes face each other, and an accommodating part is formed between the lid member and the first substrate through the second through hole;

one of the negative electrode active material and the positive electrode active material is provided in the accommodating part, and another of the negative electrode active material and the positive electrode active material is provided between the transmission membranes of the observation window; and a negative electrode collector and a positive electrode collector extend from inside of the overlapping portion and protrude outside the overlapping portion, and the negative electrode collector and the positive electrode collector are electrically connected respectively to the negative electrode active material and the positive electrode active material inside the overlapping portion.

2. The analytical cell according to claim 1, wherein the solid state joint is provided to seal at least one side of the overlapping portion.

3. The analytical cell according to claim 1, wherein the one of the negative electrode active material and the positive electrode active material provided in the accommodating part is formed into particles, and contained in a mixture electrode.

* * * * *